(12) United States Patent
Pedersen et al.

(10) Patent No.: US 12,156,642 B2
(45) Date of Patent: Dec. 3, 2024

(54) TRANSSEPTAL SYSTEMS, DEVICES AND METHODS

(71) Applicant: Boston Scientific Medical Device Limited, Ballybrit (IE)

(72) Inventors: Wesley Robert Pedersen, Minneapolis, MN (US); Paul Sorajja, Minneapolis, MN (US); William Joseph Drasler, Minnetonka, MN (US)

(73) Assignee: Boston Scientific Medical Device Limited, Ballybrit (IE)

( * ) Notice: Subject to any disclaimer, the term of this patent is extended or adjusted under 35 U.S.C. 154(b) by 73 days.

(21) Appl. No.: 17/606,592

(22) PCT Filed: Apr. 28, 2020

(86) PCT No.: PCT/US2020/030264
§ 371 (c)(1),
(2) Date: Oct. 26, 2021

(87) PCT Pub. No.: WO2020/223230
PCT Pub. Date: Nov. 5, 2020

(65) Prior Publication Data
US 2023/0371936 A1 Nov. 23, 2023

Related U.S. Application Data

(60) Provisional application No. 62/840,062, filed on Apr. 29, 2019.

(51) Int. Cl.
*A61B 17/00* (2006.01)
*A61M 25/09* (2006.01)
*A61M 29/02* (2006.01)

(52) U.S. Cl.
CPC ....... *A61B 17/00234* (2013.01); *A61M 25/09* (2013.01); *A61M 29/02* (2013.01);
(Continued)

(58) Field of Classification Search
CPC .... A61B 17/00234; A61B 2017/00247; A61B 2017/00331; A61B 2017/003;
(Continued)

(56) References Cited

U.S. PATENT DOCUMENTS 175,254 A 3/1876 Oberly
827,626 A 7/1906 Gillet
(Continued)

FOREIGN PATENT DOCUMENTS

WO 2013101632 A1 7/2013

OTHER PUBLICATIONS

Babaliaros V.C. et al. "Emerging applications for transseptal left heart catheterization" (2008) J. American College of Cardiology, 51(22):2116-2122.
(Continued)

*Primary Examiner* — Julian W Woo
(74) *Attorney, Agent, or Firm* — Nelson Mullins Riley & Scarborough LLP

(57) ABSTRACT

A transseptal system can include a guidewire, a dilator, and a deflectable sheath configured to safely deliver a puncture needle through a septal wall associated with the fossa ovalis and into a central region of the left atrium of a heart. The dilator can include a dilator nose having a first outer diameter and a dilator beveled segment, extending proximal of the dilator nose, tapering from a second, greater outer diameter to the first outer diameter. The length and interplay of the puncture needle and the dilator nose can be configured such that the puncture needle is inhibited from bending and impinging upon the left side of the atrial septum of the heart during use. A body of the guidewire can include at least one loop segment to provide stable support in the left atrium for delivery of a diagnostic or therapeutic device along its more
(Continued)

proximal portions. The deflectable sheath can position and align the dilator nose relative to the fossa ovalis.

17 Claims, 17 Drawing Sheets

(52) U.S. Cl.
CPC .............. *A61B 2017/00247* (2013.01); *A61B 2017/00331* (2013.01)

(58) Field of Classification Search
CPC ........... A61B 2017/22038; A61B 2017/22044; A61B 17/3478; A61M 25/09; A61M 29/02; A61M 29/00
See application file for complete search history.

(56) References Cited

U.S. PATENT DOCUMENTS

| | | |
|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |

(56) References Cited

U.S. PATENT DOCUMENTS

| | | |
|---|---|---|
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,320,695 B2 | 1/2008 | Carroll |
| 7,335,197 B2 | 2/2008 | Sage et al. |
| 7,618,430 B2 | 11/2009 | Scheib |
| 7,635,353 B2 | 12/2009 | Gurusamy et al. |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 7,963,947 B2 | 6/2011 | Kurth et al. |
| 8,029,470 B2 | 10/2011 | Whiting et al. |
| 8,114,110 B2 | 2/2012 | Bednarek et al. |
| 8,157,829 B2 | 4/2012 | Chanduszko et al. |
| 8,192,425 B2 | 6/2012 | Mirza et al. |
| 8,257,323 B2 | 9/2012 | Joseph et al. |
| 8,292,910 B2 | 10/2012 | Chanduszko et al. |
| 8,317,810 B2 | 11/2012 | Stangenes et al. |
| 8,337,518 B2 | 12/2012 | Nance et al. |
| 8,388,549 B2 | 3/2013 | Paul et al. |
| 8,500,697 B2 | 8/2013 | Kurth et al. |
| 8,768,433 B2 | 7/2014 | Jenkins et al. |
| 8,900,193 B2 | 12/2014 | Paul et al. |
| 8,900,214 B2 | 12/2014 | Nance et al. |
| 8,986,264 B2 | 3/2015 | Kimmel et al. |
| 8,992,556 B2 | 3/2015 | Chanduszko et al. |
| 9,131,849 B2 | 9/2015 | Khairkhahan et al. |
| 9,162,037 B2 | 10/2015 | Belson et al. |
| 9,326,756 B2 | 5/2016 | Stangenes et al. |
| 9,357,039 B2 | 5/2016 | Conner et al. |
| 9,533,120 B1 | 1/2017 | Kimmel et al. |
| 9,585,692 B2 | 3/2017 | Kurth et al. |
| 9,700,351 B2 | 7/2017 | Maisano et al. |
| 9,717,523 B2 | 8/2017 | Feng et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McLntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Molante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |

(56) References Cited

U.S. PATENT DOCUMENTS

| | | |
|---|---|---|
| 2006/0276710 A1 | 12/2006 | Krishnan |
| 2007/0005019 A1 | 1/2007 | Okishige |
| 2007/0060879 A1 | 3/2007 | Weitzner et al. |
| 2007/0066975 A1 | 3/2007 | Wong et al. |
| 2007/0088355 A9 | 4/2007 | Auth et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0125802 A1 | 5/2008 | Carroll |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0087261 A1 | 4/2011 | Wittkampf et al. |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0188108 A1 | 7/2014 | Goodine et al. |
| 2014/0206987 A1 | 7/2014 | Urbanski et al. |
| 2014/0296769 A1 | 10/2014 | Hyde et al. |
| 2014/0371676 A1 | 12/2014 | Leeflang et al. |
| 2015/0173794 A1 | 6/2015 | Kurth et al. |
| 2016/0022962 A1 | 1/2016 | Beissel et al. |
| 2016/0089180 A1 | 3/2016 | Entabi |
| 2016/0175009 A1 | 6/2016 | Davies et al. |
| 2016/0220741 A1 | 8/2016 | Garrison et al. |
| 2017/0189113 A1 | 7/2017 | Urbanski et al. |
| 2017/0296781 A1 | 10/2017 | Sapir et al. |
| 2019/0015644 A1 | 1/2019 | Thomspon et al. |
| 2019/0021763 A1 | 1/2019 | Zhou et al. |
| 2019/0247035 A1 | 8/2019 | Gittard et al. |

OTHER PUBLICATIONS

Farley M.J. "How to perform a transseptal puncture" (2009) Heart, 95:85-92. doi: 10.1146/hrt.2007.135939, Downloaded from heart.bmj.com on Jun. 16, 2009.

Patent Corporation Treaty, International Search Report for PCT Application No. PCT/US2020/030264, mailed on Aug. 27, 2020.

Patent Corporation Treaty, Written Opinion for PCT Application No. PCT/US2020/030264, mailed on Aug. 27, 2020.

Earley M.J. "How to perform a transseptal puncture" (2009) *Heart*, 95:85-92. doi: 10.1146/hrt.2007.135939, Downloaded from heart.bmj.com on Jun. 16, 2009.

International Preliminary Report on Patentability received for PCT Patent Application No. PCT/US2020/030264, mailed on May 27, 2021, 29 pages.

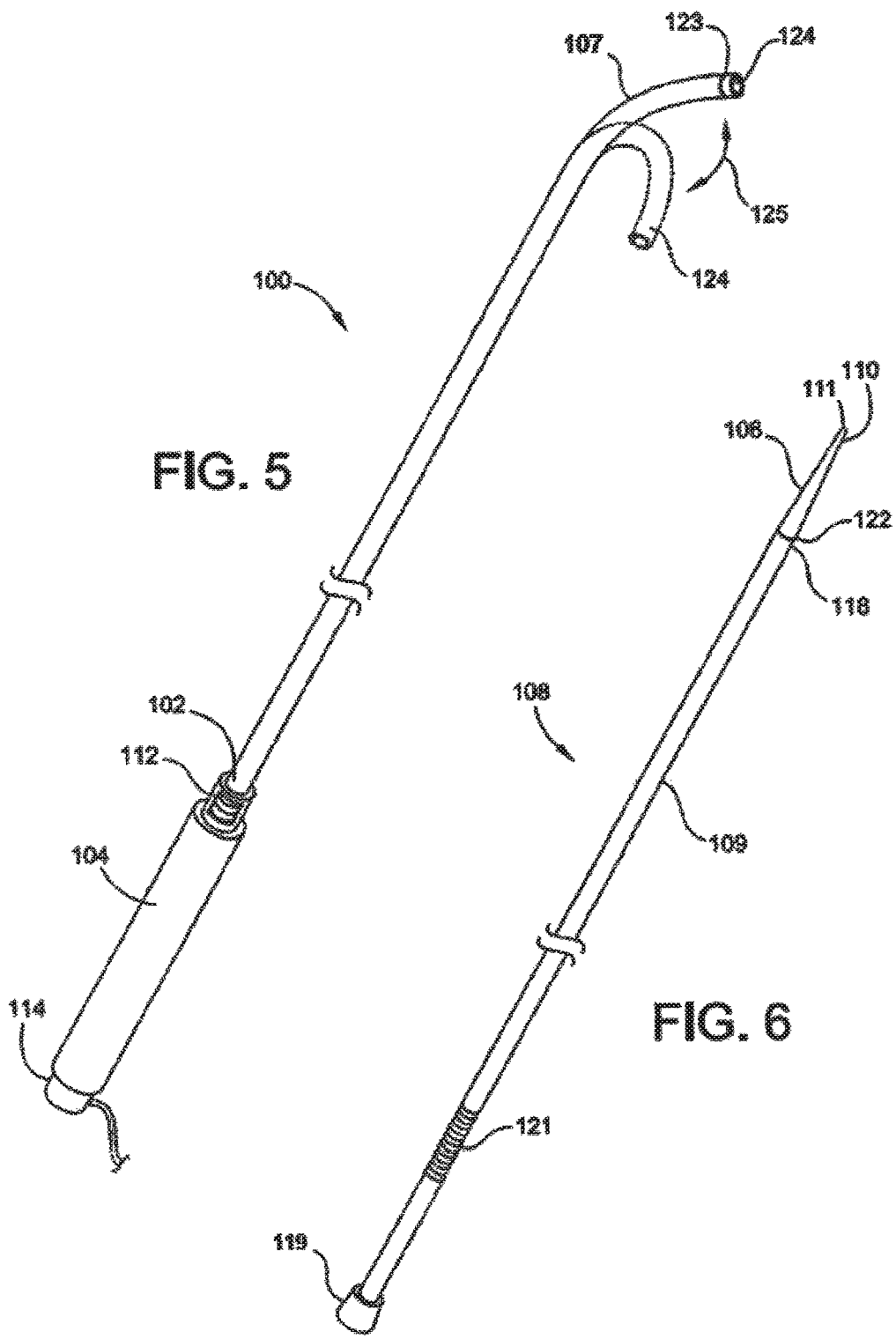

TRANSSEPTAL SYSTEMS, DEVICES AND METHODS

CLAIM OF PRIORITY

Benefit of priority is hereby claimed to U.S. Provisional Patent Application Ser. No. 62/840,062, entitled "TRANSSEPTAL GUIDEWIRE NEEDLE TIP" and filed on Apr. 29, 2019, which is herein incorporated by reference in its entirety.

TECHNICAL FIELD

The present subject matter relates to, among other things, medical devices for accessing left heart structures by way of crossing a septum of a heart.

BACKGROUND

Transseptal punctures can be used to access the left atrium (LA) of a heart by way of the right atrium (RA). Access to the LA is commonly required for atrial fibrillation ablation treatment and, more recently, treatment of valvular and other structural heart diseases, for example.

ABBREVIATIONS

Unless otherwise noted, the following abbreviations apply throughout this disclosure:
FO: fossa ovalis 202
Fr: French (increments for catheter sizing diameter)
GW: guidewire 10
LA: left atrium 208
LAA: left atrial appendage 210
MRI: magnetic resonance imaging
MV: mitral valve 212
RA right atrium 206
TEE: transesophageal echocardiography
TTE: transthoracic echocardiography

OVERVIEW

The present inventors recognize that transseptal puncture systems and devices should be able to locate specific locations on the fossa ovalis (FO)—a depression on the right side of the atrial septum between the RA and LA of a heart— reliably to safely and accurately puncture the septal wall for a given procedure. Inadvertent puncturing of structures such as the aorta, left or right atrial free wall or pulmonary vein can result in cardiac perforation and tamponade. In addition, some left heart procedures require that highly specific septal wall sites associated with the FO be traversed to pinpoint specific targets for diagnostic or therapeutic device positioning.

The present inventors further recognize that existing transseptal puncture systems and devices suffer from drawbacks, including but not limited to: (1) difficulty engaging with precision and stability on specific locations of the FO; (2) difficulty with needle advancement across the septal wall; (3) difficulty dealing with a redundant or aneurysmal septum leaving the apex of a tented needle on the FO, adjacent to the LA free wall and thus at risk for perforation and pericardial tamponade; and (4) difficulty dealing with prior septal occluder placement necessitating alternative puncture locations on the native septum or direct occluder puncture.

The present subject matter is directed to, among other things, achieving transseptal puncture in a highly efficient and safe manner both to gain access to the LA by way of a guidewire (GW) including a distal needle segment, a mid-looped or coiled left-atrial segment, and one or more linear elongated proximal segments, and to serve as a platform for structural or other device delivery to the LA of the heart. Specifically, the present subject matter is directed in part to a transseptal GW 10 incorporated with a transseptal puncture needle 12. The GW 10 can comprise a relatively stiff proximal segment end 16 and a middle loop segment 14, wherein the distal end 22 comprises the junction with the transseptal needle 12. One or more mid-segment GW loops 24, 26 can come to rest in the LA 208. The middle loop segment 14 can be formed of a shape memory material to form at least two looped segments, for example—a second more distal, usually outer, broad coil 24 and a first more proximal, inner coil 26, wherein the middle segment 14 can be in continuity with the elongated linear stiff GW segment 16 at proximal end 25, which eventually rests externally for exchanges.

The present subject matter is further directed to a transseptal GW puncture system that can traverse the FO 202, comprising a GW 10, a transseptal dilator 108, and a sheath 100. The distal end of the GW 10 can comprise a transseptal needle 12 attached to the looped GW segment 14 at its distal end 22 and in turn can be positioned in continuity with the distal end 17 of the linear, stiff GW segment 16. The transseptal needle 12 can have shape memory at the point of attachment to the looped GW segment 14, wherein the shape memory is sufficient to have the transseptal needle 12 retain a pre-specified angle with respect to the looped GW segment 14 to maintain atraumatic stability within and central to the loops 24, 26. One or more of the loops 24, 26 can be positioned and stabilized in the LA 208 resting adjacent to an inner surface of the LA 208. The middle looped segment 14 can be formed of a shape memory material to form the two loops 24, 26, wherein the proximal end 25 of the more proximal coil 24 is in continuity with the proximal elongated stiff segment of the GW 16, and wherein a secondary bend 29 can be positioned in the RA 206 transitioning into the elongated, linear proximal most segment of the GW 10.

The transseptal dilator 108 can comprise an elongated catheter 109 which rests within the sheath 100, tapering down to a narrowed dilator distal segment 110, wherein the catheter lumen 111 throughout remains compatible with the GW 10, which may have a full spectrum of diameters ranging from 0.021-0.035 in, inclusive, or more. At some point along the distal segment 106 can be a radiopaque marker 122 positioned to be overlapped with a radiopaque tip marker 123 on the sheath 100 when at that point the transseptal dilator 108 and sheath 100 are of equivalent external diameters. The dilator 108 can be advanced forward into a precise position on the FO 202 for "tenting" the FO 202 by way of a series of forward movements of the actuator 112 adjacent to the distal end of the handle 104. Steerable maneuvers on the proximal sheath handle 104 can permit antegrade and retrograde flexion, and torqueing anterior or posterior of the entire sheath 100 can be carried out to position the distal end 124 of the sheath and the retained dilator tip 110 adjacent to the specific FO site for a specific procedure. Advancement and retraction movements of the dilator distal segment 110 relative to a stabilized sheath 100 with the use of the actuator 112 on the proximal sheath 100 can interact with the proximal end 119 of the dilator 108.

Once the FO 202 is tented with the dilator 108 which contains the transseptal needle 12, the needle 12 can be advanced, puncturing the FO septum 202 and crossing into the LA 208. The transseptal needle 12 can fold or bend from shape memory at a discrete angle at the hinge point 20 on the coiled GW segment 14 to which it is connected after being advanced across the FO 202. It can form an angle which may range from about 45-140 degrees, inclusive. Further advancement of the transseptal GW 10 can position the looped section 14 coils of the GW 10 within the LA chamber 208 aiding also in preserving the needle position atraumatically in the central LA 208 by way of remaining central to the loops. Preferably, the GW coils 24, 26 have a small inner diameter coil 26 and larger outer diameter coil 24 aiding in preserving the needle 12 central to the LA 208. The smaller in diameter inner coil can prevent needle 12 damage to the tissue in the LA wall. In another embodiment, the coils 24, 26 may be of equal diameters.

In another embodiment, the coils 24, 26 can be offset, as illustrated in FIGS. 3 and 4, to further aid in preserving a central location of the needle 12 which can also be folded in a third dimension, an additional feature making it less susceptible to perforating LA 208 structures when the folded distal transseptal needle 12 is advanced and deflected medially further aiding in maintaining a central needle 12 position within the offset but equal spaced loops 14. Coils 24, 26 can be offset by approximately 0.75-2 cm, inclusive. The coils 24, 26 can be intermediate in stiffness allowing for less traumatic interaction with the LA free walls. A secondary bend 29 in the right atrial GW segment can aid in preserving a perpendicular trajectory across the FO 202 and co-axially in the WC 215. The elongated, proximal stiff GW segment 16 can have a length of 260 cm, for example, but may be significantly longer for purposes of catheter or device exchange.

The forward positioning of the system of the present subject matter allows for precise positioning of the distal sheath for precise device positioning thereby establishing ideal LA 208 positioning ultimately dictated by the specific left heart target for a given device, i.e., LAA 210, MV 212. The system is intuitive and simple to accurately position on a specific FO 202 target by using iterative dilator advancement under echo or other imagining guidance. After the coils have been advanced across the FO 202 and secured in the LA 208, the dilator 108 can then be advanced over the coiled GW 10 into the LA 208 preserving the overlapping radiopaque segments in place until the sheath 100 has crossed into the LA 208. Overlapping radiopaque markers 122, 123 on the distal dilator end 106 and sheath tip 124 can be used to confirm that they are at equivalent diameters for smooth simultaneous advancement of the dilator 108 and sheath 100 across the FO 202.

The deflectable and steerable nature of the sheath 100 can permit the sheath 100 to obtain the directionality, angulation and reach using a single size forward looking catheter system for the variety of RA 206 sizes and FO 202 angles in various patient-specific anatomy.

The collective system preferably includes a needled GW 10 delivered by the "one size fits all" catheter system for iteratively advancing the dilator 108, containing the retracted needle 12, into a precise tenting position on the FO 202. An actuator 112 on the sheath 100 adjacent to the handle 104 can permit highly controlled advancement of the distal segment 110 for "tenting" the FO membrane prior to needle puncture. The actuator 112 can be advanced or retracted with the operator's thumb without removing the operator's hand from the rotatable handle 104. The dilator 108 may have a more flexible distal segment to permit smooth tracking over the coiled GW segment in the LA 208.

The deflectable sheath tip 124 may have monopolar or bipolar directionality. The deflectable sheath 100 can, for example, have a distal fixed 2 degree bend within the RA 206 which may range from 2-20 degrees, inclusive, to more easily establish perpendicularity to the FO 202. Standard, commercially available sheath dilator catheters may also be used in combination with the previously described novel needle GW.

Advantageously, the present subject matter provides a system and device that satisfy the following: (1) improved ease of use; (2) intuitive manipulation for precise distal control; (3) improved device and procedural efficacy; (4) increased device safety across a wide range of operator skills; (5) enhanced workflow and decreased procedural times; and (6) decreased procedural costs secondary to a combined needle GW.

These and other examples and features of the present subject matter will be set forth, at least in part, in the following Detailed Description. This Overview is intended to provide non-limiting examples of the present subject matter—it is not intended to provide an exclusive or exhaustive explanation. The Detailed Description below is included to provide further information about the present subject matter.

BRIEF DESCRIPTION OF THE DRAWINGS

In the drawings, like numerals can be used to describe similar features and components throughout the several views. The drawings illustrate generally, by way of example but not by way of limitation, various embodiments discussed in the present patent document.

FIG. 5 is a side plan view illustrating a representative deflectable sheath for use with the needle-GW of the present subject matter.

FIG. 6 is a side plan view illustrating a dilator for use with the deflectable sheath of FIG. 5.

Figure 1:
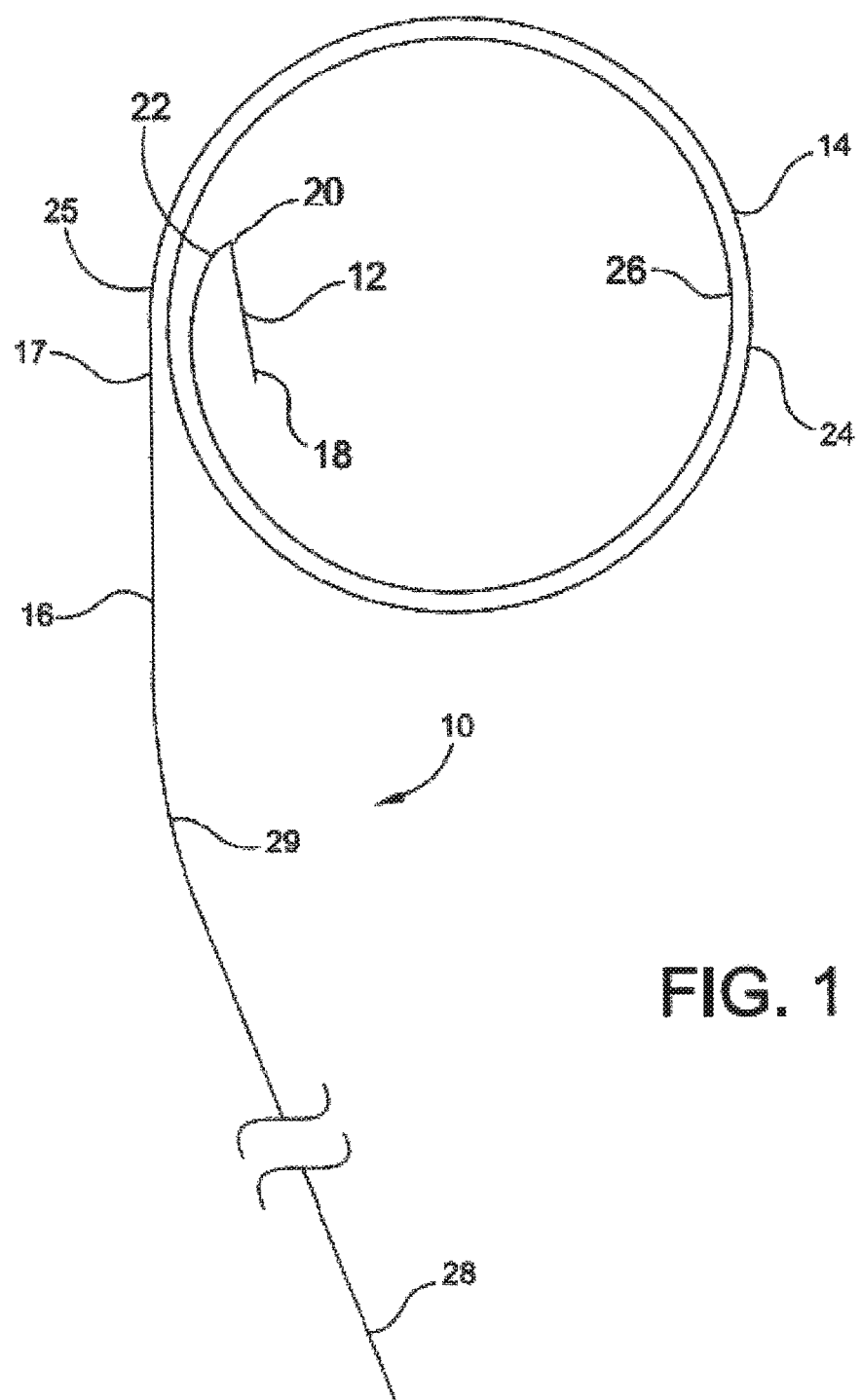
FIG. 1 is a side plan view of a first embodiment of the present subject matter of the combined transseptal needle and GW.
Figure 2:
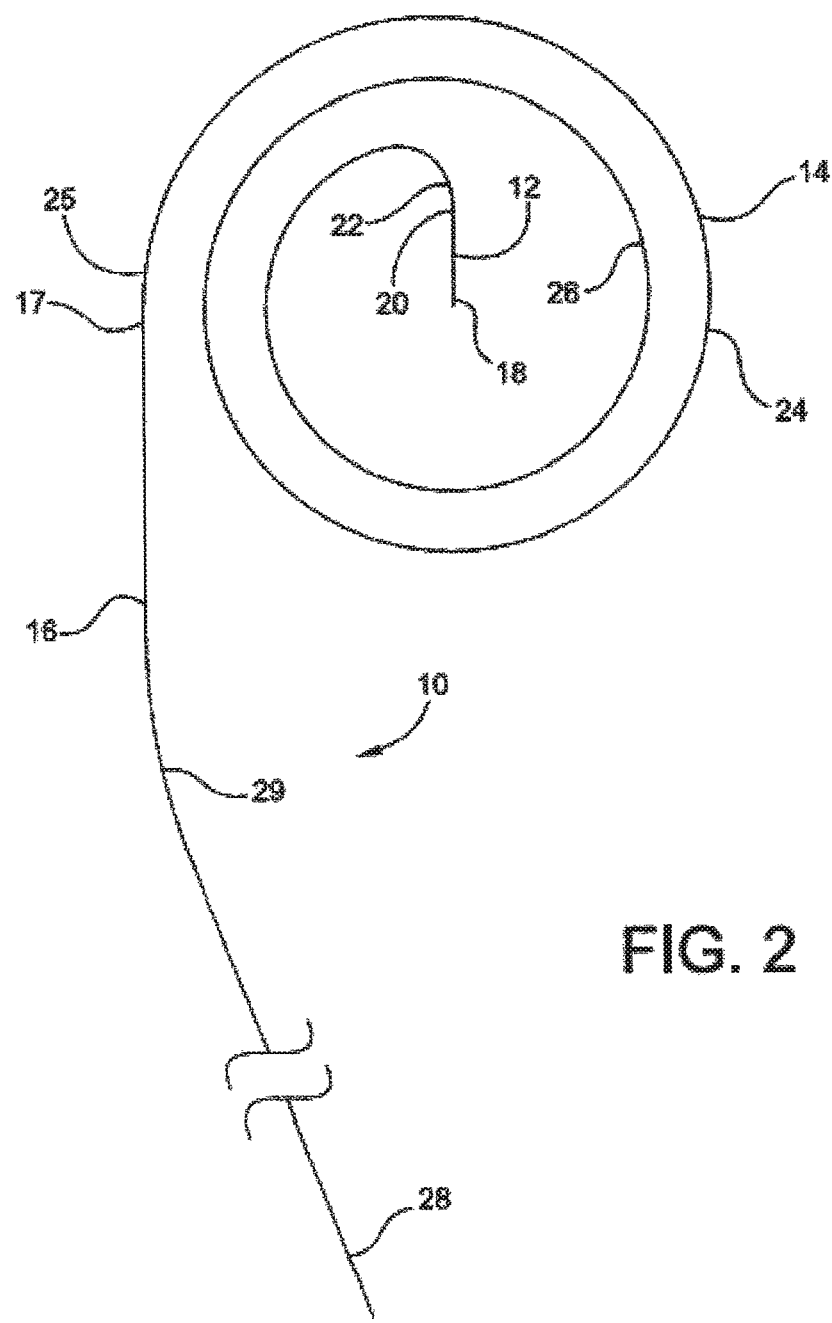
FIG. 2 is a side plan view of a second embodiment of the combined transseptal needle and GW of the present subject matter.

The drawing figures are not necessarily to scale. Certain features and components may be shown exaggerated in scale or in schematic form and some details may not be shown in the interest of clarity and conciseness.

DETAILED DESCRIPTION

With reference to the guide number in the drawings, the transseptal puncture system of the present subject matter is preferably, but not limited to, a "one size fits all" system whereby a single-sized system may be used in a variety of anatomical configurations and atrial sizes. The system includes specialized components, including an exchange GW with a distal transseptal needle and adjacent coils or loops for GW securement in the LA 206. In addition, the system may include a dilator which interacts with an actuator on a proximal sheath handle for controlled positioning on the FO aided by the deflectable sheath.

Guidewire 10

Reference is now made to FIGS. 1-4 illustrating a transseptal needle-GW 10. The transseptal needle-GW 10 can be an integrated component that can avoid the need for a separate transseptal needle and multiple GW exchanges, lengths and curves to treat various anatomies. The transseptal needle-GW 10 can have at least three defined segments: (1) a distal transseptal needle 12; (2) a middle or looped LA segment 14; and (3) a proximal elongated linear, stiff segment 16.

Needle 12

The transseptal needle 12 can be positioned in continuity with the distal end 22 of the GW loop segment 14. The transseptal needle 12 is preferably relatively short, with a length between about 0.75-2.0 cm, inclusive. The needle 12 can have an ultra-low profile tip 18. The proximal end 20 of the needle 12 can be in continuity with the adjacent distal loop segment 14, which can be configured to be linear when retained in the central lumen 111 of a dilator tip prior to advancement.

The transseptal needle 12 can have a lubricious coating to minimize resistance and a sharply tapered tip 18 to puncture and easily transition across the FO 202 (illustrated in FIG. 8), including those that may be densely scarred or aneurysmal. Inadvertent needle lurching across the FO membrane and loss of a preferred puncture site can be avoided by the extra-fine point on the needle tip 18 and slow iterative delivery of the forward-looking tapered transseptal dilator 108 into the FO 202 for stable positioning and "tenting" of the membrane by the dilator tip 18 which is in turn supported by a deflectable transseptal sheath 100. With this forward looking system, unintended anterior or posterior torqueing forces resulting in sliding across the FO 202 can be greatly minimized.

The transseptal needle 12 can preferably be composed of a metallic material, such as stainless steel or alloy including Nitinol with shape memory, and can be attached to the GW loop segment 14, for example, with a weld or possibly interdigitating slots which interact to form a more stable, yet flexible, union allowing the needle to fold on itself thereby avoiding puncturing the LA free wall, the pulmonary vein, etc. Other means of creating a pre-shaped angle between the needle 12 and loop segment 14 can also be conceived and utilized.

The transseptal needle 12 can sharply angle at a proximal end/hinge point 20 where it connects to the distal end 22 of the looped GW segment 14, having retained a pre-specified angle central to the LA loop segment 14, thus maintaining atraumatic stability within the central LA loop segment 14 and preventing contact and possible perforation of LA 208 structures including a pulmonary vein, LA free wall and LAA 210.

Following the GW advancement and transseptal puncture, the needle 12 can abruptly flex centrally, preferably at an acute angle with the adjoined looped GW segment 14, as illustrated in FIGS. 1-4. The needle 12 can remain linear after entering the LA 208 but flexes inward, preferably at an angle of about 45-140 degrees, inclusive, relative to the distal looped GW segment 14. The diameter of the transseptal needle tip 18 can be ground down to an ultra-low profile and tapered back to conjoin the distal loop segment 14, most likely transitioning to a profile in the range of 0.021-0.035 in, inclusive, or greater.

Guidewire Loop Segment 14

Figure 3:
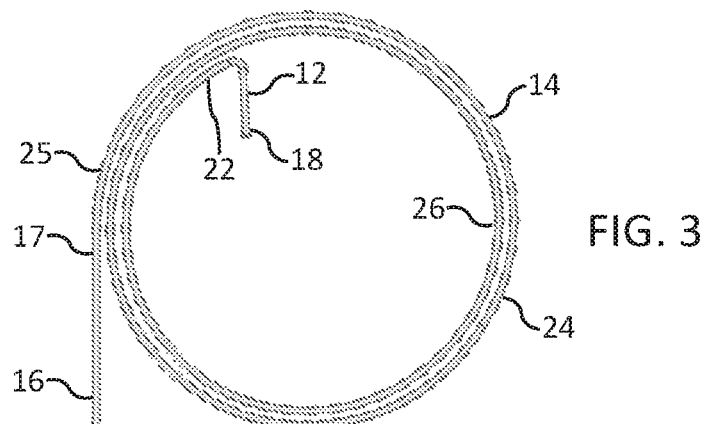
FIG. 3 is a side plan view of a third embodiment of the present subject matter of the combined transseptal needle and GW with offset loops.
Figure 4:
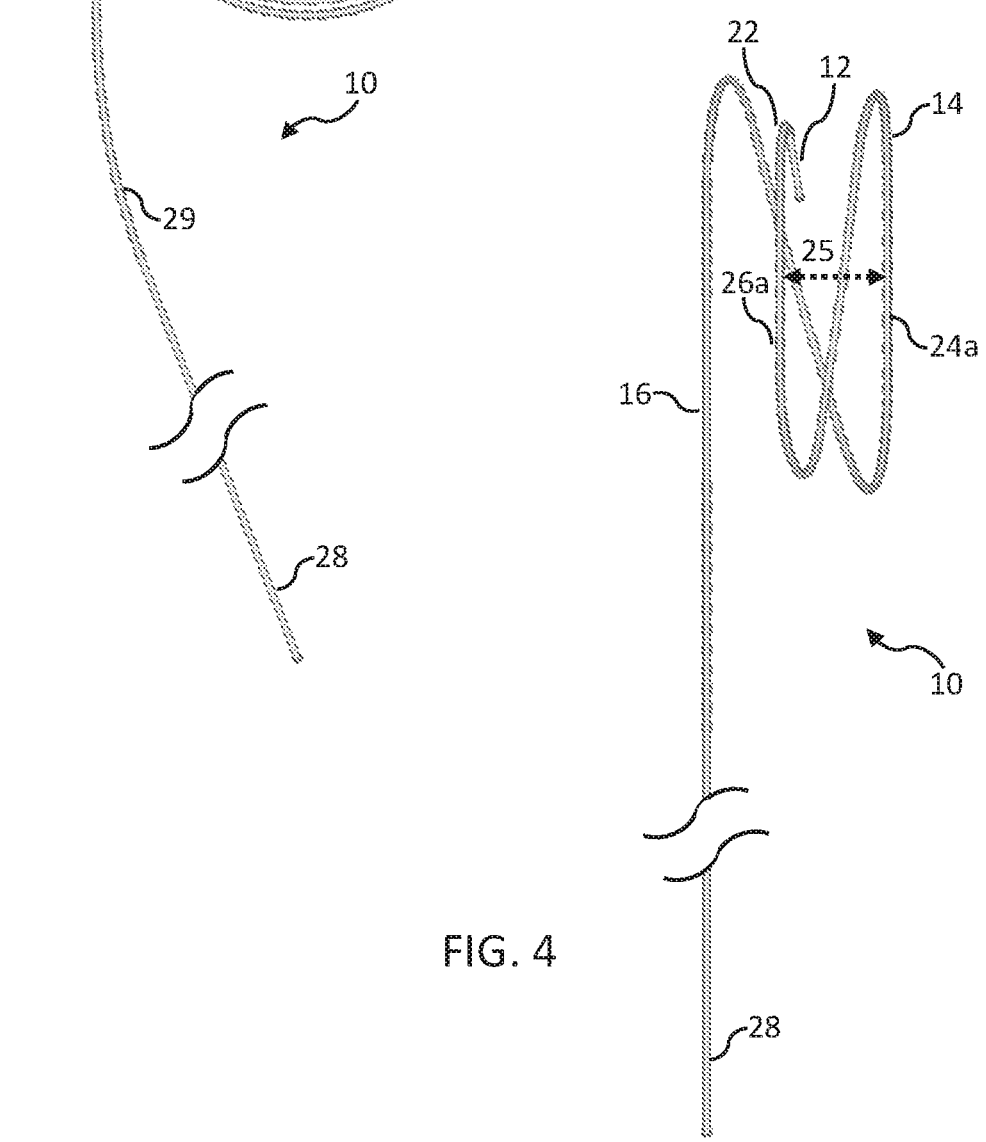
FIG. 4 is a front plan view of the transseptal needle of FIG. 3, which has been rotated ninety degrees.

The looped GW segment 14 can be designed to stabilize the GW 10 position atraumatically in the LA 208 and, in addition, assists in protecting the left atrial free wall from unwanted needle puncture. Two or more looped segments 24, 26 may typically range between about 2.5-4.0 cm, inclusive, in diameter and be formed by shape memory as it exits from a transseptal dilator 108 into the LA 208. The distal GW looped segment 14 in one embodiment can be formed by two roughly equal in size circular or non-circular loops in a plurality of shapes which are again formed upon deployment in the LA chamber, as illustrated in FIGS. 3-4.

The coils provide at least four useful functions:
1. The coils can confirm the correct LA chamber positioning by taking on the unconstrained, known shape within the LA 208.
2. The coils 14 can maintain stable positioning in the LA 208 to avoid inadvertent withdrawal of the GW 10 into the RA 206 or forceful needle tip 12 advancement into the LA free wall or pulmonary vein.
3. The outer broad coil 24 can provide a longer GW support ramp over which the dilator 108 and sheath 100 can be advanced with less resistance into the LA 208 around the curve to facilitate catheter support.
4. The coils can form an outer protective shield in which the centrally positioned needle 12 is kept at a safe distance from penetrating LA 208 structures.

In another embodiment, there are at least two circular coils, the inner coil 26 diameter being smaller than the outer coil 24 diameter, as illustrated in FIGS. 1-4, the inner coil thus central to the outer coil 24. In this embodiment, the larger, outer coil 24 can be compressed by LA 208 structures in the absence of any conformational change of the inner coil 26 thus further protecting deformity of the distal needle 12 and preserving its central location. As an example, the inner coil 26 of the GW 10 may have a diameter between about 1.5-3.0 cm, inclusive, such as about 2.5 cm. The outer coil 24 can have a diameter between about 3.0-4.0 cm, inclusive, such as about 3.5 cm.

In a third embodiment, the two coils 24, 26 can have parallel portions 24a and 26a, be unequal in diameter, and be offset by about 0.75-2.0 cm, inclusive. Further, a second preformed bend at the junction of the distal transseptal needle 12 and the GW loop segment 14 in the third dimension central to the two offset wire coils 24, 26 can be incorporated, as illustrated in FIG. 5. Its purpose is to further aid in preventing needle perforation of the LA 208 by allowing the needle 12 to not only be centered circumferentially in two dimensions upon flexion with this embodiment but the needle 12 can be directed centrally in a third dimension between the breadth of two offset loops 24, 26. The distance between the parallel portions 24a and 26a of coils 24, 26, as illustrated by dotted line 25, can be about 1 cm, for example, and may range from about 0.75-2.0 cm.

Proximal Guidewire Segment 16

The proximal GW segment 16 can be in continuity with the adjacent coil segment 14 at the distal end 17 of the segment 16. The proximal GW segment 16 can include a proximal free end 28, which is externalized with adequate length to permit catheter or device exchange while preserving the distal GW loop segment 14 positioned in the LA. The distal end 17 of the proximal GW segment can transition linearly across the atrial septum into the LA 208. There can then be a shallow fixed second degree bend 29 roughly in the mid-RA 206, retaining a preferable angle of 2° to 20°, inclusive. The elongated proximal stiff GW segment 16 extends from most distal end of the long proximal segment 17 to the most proximal end 28 having a preferred diameter of 0.021-0.035 in, inclusive. The long proximal stiff GW segment 16 may extend from 240-300 cm, inclusive, preferably 260 cm in length. This long, stiff GW segment 16 can serve as a supportive rail for exchanging an array of catheters and devices for delivery to left heart targets.

Sheath 100

Referring to FIG. 5, the transseptal delivery sheath 100 can be a unipolar or bipolar, for example, deflectable sheath actuated with a rotatable proximal ergonomic handle 104 for superior/inferior flexion, and one-to-one sheath torque control for optimal anterior/posterior positioning. Advancement or retracting of the transseptal sheath 100 can permit superior and inferior positioning for controlled, atraumatic guidance in all planes. The sheath 100 can have a proximal end 102 located adjacent the actuator 112 and a distal segment 107. Current transseptal systems designed for commercial use are brought into the FO 202 using a clockwise torque of the sheath/dilator system generally from a femoral vein access sight that may be overly aggressive (excessive in length) which may in turn result in inadvertent "stored up" torque if the over-reaching dilator 108 momentarily "catches" distally on an atrial septum prominent ridge. Further efforts to position the dilator distal segment 110 within the FO 202 may result in perforation of the RA 206 free wall or appendage. Conversely, a dilator 108 of insufficient length or "reach" and inability to engage the membrane across the FO 202 results in an inability to puncture the FO 202.

The sheath 100 can have an ergonomic two-way rotatable handle 104 for superior and inferior distal sheath flexion, illustrated by arrow 125 and reach at the tip 124 of the sheath 100. In addition, 1:1 torque transfer distally in an anterior to posterior position can be accomplished through wire braid reinforcement (not illustrated) of the sheath 100, which can also improve back up support for enhanced device delivery. The sheath 100 can initially be positioned adjacent to but without engagement of the atrial septum using fluoroscopic and TEE guidance and when available, possibly real time MRI and computer tomography.

Once the sheath 100 is accurately positioned at the appropriate short distance from the FO 202 (e.g., about 0.5-2.0 cm) in the RA 206 under imaging guidance, the dilator 108 can be advanced while keeping the sheath 100 stationary. The sheath handle 104 and adjacent actuator 112 for the dilator can permit system (sheath and dilator) manipulation with one hand kept in position without need for use of the operator's contralateral hand. The actuator 112 for the dilator 108 can be manipulated by the operator's thumb or other digit for iterative forward advancement or retraction by interacting with the frictional elements 121 on the dilator 108. The wire-braid, reinforced sheath 100 can provide strong backup, kink-resistant support for advancing the distal segment 110 of the dilator 108 and subsequently the dilator 108 into a precisely controlled specific location of the FO 202 for "tenting" of the membrane.

The sheath 100 preferably includes but does not necessitate a dilatable shaft to accommodate highly variable device profiles; on the other hand, a series of fixed diameter sheaths may be used to accommodate a variety of device profiles. Ideally expandable or dilatable sheaths, ranging from about 8.5 Fr to potentially up to 30 Fr, inclusive, could eliminate the need for keeping multiple sheath diameters available for different procedures. One embodiment is thus a single sheath size which is conformed to be dilatable across a range of diameters. Transseptal sheaths which may require delectability at two or more distances from the proximal handle may be preferred for device delivery around complex or multiple curves.

A plurality of other supportive structures may run linearly within the sheath body to preserve an adequate level of support for subsequent device delivery across more angulated anatomy. A 2-20 degree secondary bend, for example, may be positioned proximal to the more distal deflectable bend which can aid in achieving a more perpendicular angle at the FO for strong coaxial backup support. In addition, this can permit distal flexion greater than 180 degrees, which may on occasion be needed to achieve appropriate sheath positioning within the medial aspects of the left heart. A tight hemostatic valve on the sheath hub 114 can minimize back bleeding around the GW 10, including those with diameters down to 0.021 in, for example. Preferably, the sheath 100 is 90 cm long (70 cm usable length) or longer. Hubs for locking the dilator to the sheath may be incorporated.

Dilator 108

The transseptal dilator 108 can have an ultra-low-profile distal segment 110 with a reverse taper back, illustrated at 106, to a fixed external diameter 118 at the distal end of the dilator 108, compatible with the internal sheath diameter. The dilator 108 can be advanced in a forward motion until "tenting" of the FO membrane is demonstrated in a precise position specific to the position visualized by TEE or other real time imaging detectors specific to the procedure being performed.

In a preferred embodiment, the dilator 108 can interact with the actuator 112 adjacent to the sheath handle 104 by way of a frictional contact element 121 or use of interlocking gears for precise gentle control of the dilator movements. An actuator 112 that permits advancement or retraction of the dilator will preferably be controlled with the ipsilateral thumb, preserving the ability to maneuver both the dilator 108 and sheath handle 104 with one hand. The dilator 108 can have variable flexibility along its length, with a more flexible distal segment 118 to prevent excessive straightening or movement of the catheter system as it is advanced over the GW looped segment 14.

The dilator distal segment 106 should be able to be advanced beyond the stationary distal sheath 100, preferably up to about 5 cm, although it may be altered to extend beyond the sheath tip from about 3.0-8.0 cm, inclusive, for example. This allows controlled advancement of the dilator 108 across the FO 202 and into the LA 208 over the distal GW 10. After the septal puncture and advancement of the dilator 108 into the LA 208, while maintaining the sheath 104 fixed in the RA 206, there should be ample space until the radiopaque markers 122, 123 overlap in the RA 206 side of the septum following which the composite system with transseptal dilator 108 and sheath 100, having flush external diameters, are now able to be advanced into the LA 208 as a single unit. The dilator distal segment 106 ends in a low profile tip 110 and can have a radiopaque marker 122 proximal to the dilator distal segment 106 matching the profile of the radiopaque marker 123 on the sheath tip 124 rendering a point of smooth transition between the two for simultaneous advancement across the FO 202 preventing "hang-up" of the sheath tip edge on the atrial septal crossing point.

Method of Use

Figure 7:
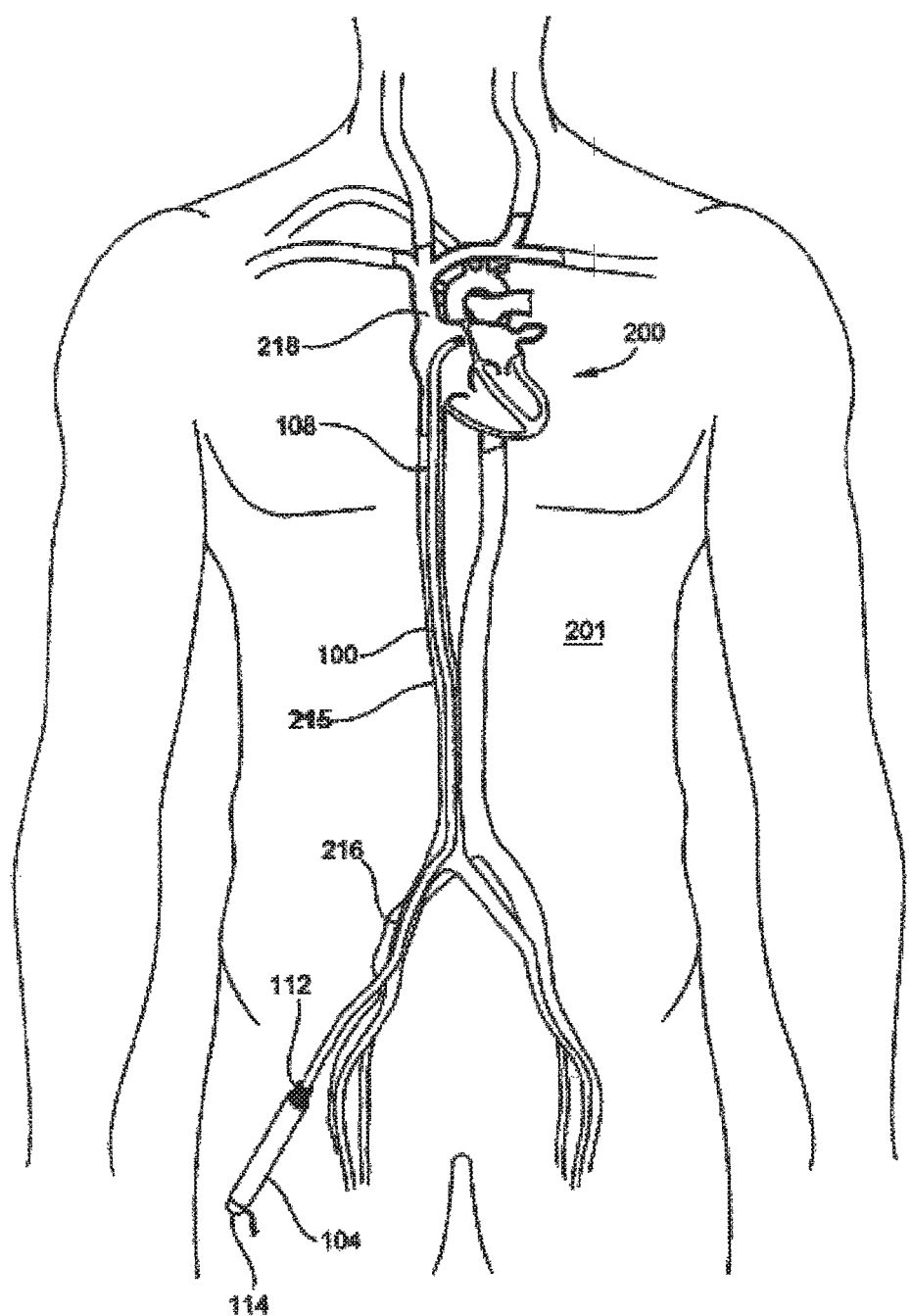
FIG. 7 is a front view schematic representation of the human central venous circulatory system including the heart and venous system with a deflectable sheath of the present subject matter.
Figure 8:
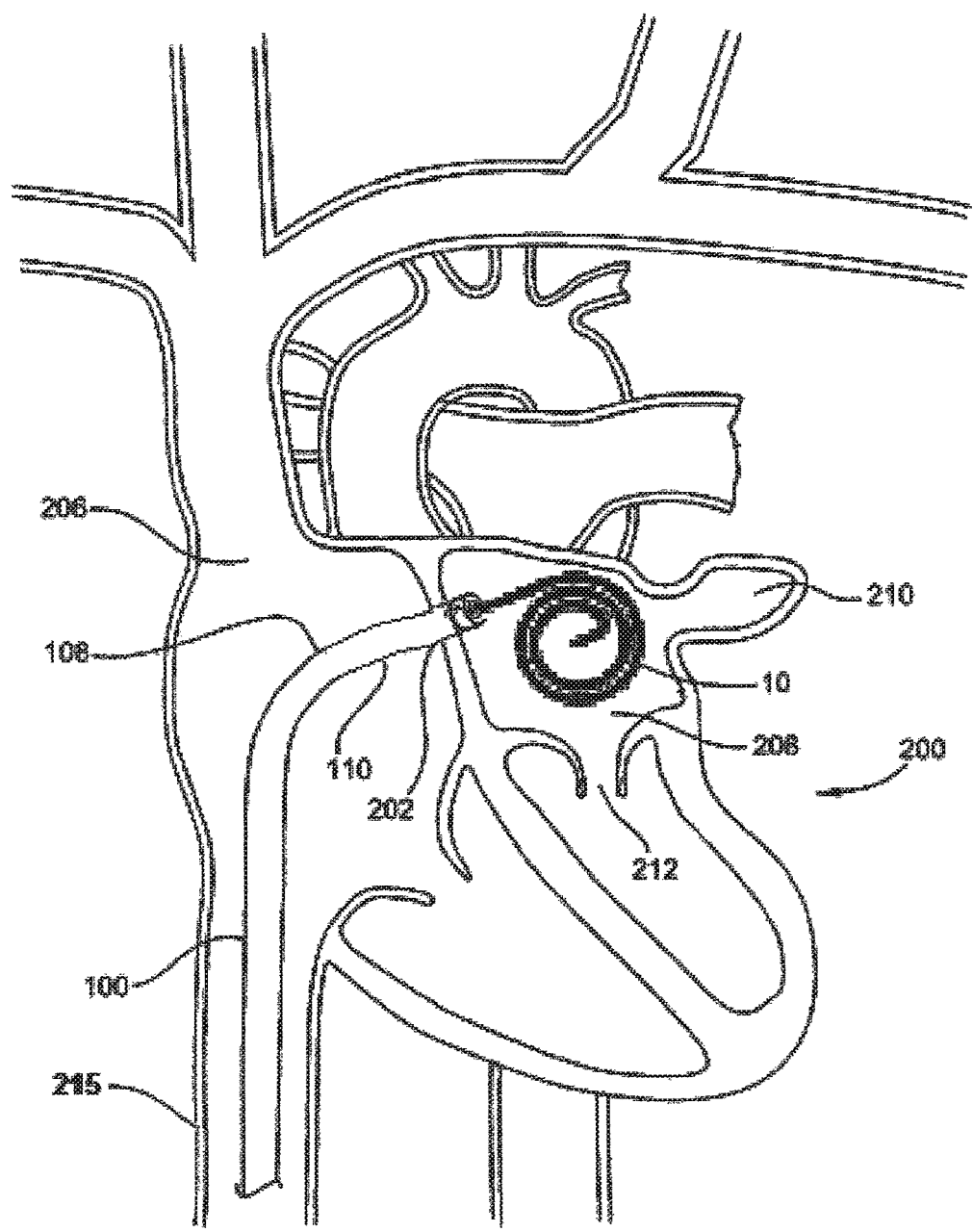
FIG. 8 is a front view schematic representation of a cross-section of the human heart with the deflectable sheath positioned across the atrial septum and positioned in the LA with the distal needle GW loops in the LA.

Referring to FIGS. 7 and 8, an exemplary method of operation can be as follows on a human patient 201. As described below, this technique generally is guided by TEE or TTE supplemented with standard fluoroscopy. It should be understood that the procedure could also be guided by intra-cardiac echo, real-time MRI or image integration with pre-procedural volume rendered computer tomography images. This later imaging method uses standard fluoroscopic images to which the pre-acquired computer tomography images may be oriented and superimposed on for guidance. Reference is made to U.S. Pat. No. 8,900,214 to Nance et al., which is incorporated herein for a general description of human anatomy, including the heart 200, and insertion of a transseptal sheath 100 into the atrial region.

A 0.032 in J-tipped GW is advanced from the right femoral vein 216 into the superior vena cava 218 using fluoroscopy. The deflectable sheath 100 and dilator 108 are advanced as a unit over the J-tipped GW 10 and positioned in the mid RA 206. The J-tipped GW 10 is removed and the dilator 108 is flushed. The distal tip 18 of the GW 10 is then advanced into the 0.032 in compatible dilator 108 under fluoroscopy and the distal tip 18 of the GW 10 is positioned just proximal to the dilator distal segment 110.

The ergonometric handle 104 on the sheath 100 is oriented axially to permit the deflectable tip 124 to be ante-flexed toward the FO 202. One to 3 cm of the dilator 108 is advanced distal to the fixed sheath 100 fluoroscopically and echocardiographically prior to maneuvering the sheath 100 toward the FO 202. To accomplish this anterior or posterior orientation, the sheath 100 is torqued anteriorly or posteriorly. The sheath 100 is advanced or withdrawn to gain a more superior or inferior position. Once again, the proximal sheath handle 104 is turned to flex the distal tip 124 to a superior, i.e., retrograde, or inferior, i.e., antegrade, trajectory. A TEE probe is most commonly used for optimal imaging of the FO 202 and adjacent dilator distal tip 110 using orthogonal views: bicaval view for superior-inferior orientation and short axis view at the aortic level to demonstrate anterior-posterior positioning. Using these TEE views, a precise position on the FO 202 for a procedure specific puncture can be obtained. The actuator 112 adjacent to the sheath handle 104 is used to slowly and iteratively advance the dilator tip 110 creating "tenting" within the FO 202 and the correct position confirmed by TEE. If the dilator distal tip 110 is incorrectly positioned, the dilator 108 can be withdrawn with the actuator 112 and redirected after manipulating the sheath 100.

With correct positioning confirmed using the tenting position, the GW 10 proximal end is advanced and the needle tip 18 punctures and crosses the FO 202 membrane. As the GW 10 is further advanced, the needle 12 flexes sharply at the hinge point 20 where it is attached to the loop segment 14 of the GW 10. As the GW 10 is still further advanced, its distal coils 14 are self-positioned in the LA 208 and the needle 12 is kept flexed central to the coils 24, 26. Catheters are always aspirated and flushed with exchanges. The patient is therapeutically heparinized as soon as the GW loop segment 14 is advanced into the LA. Correct positioning of the GW 10 is confirmed by verifying its preformed shape. The coiled or looped segment 14 can take on several different embodiments as noted herein. The dilator 108 is advanced over the coiled wire maintaining the sheath 100 in a fixed position within the RA 206.

With the appropriate length of dilator 108 advanced under fluoroscopy, the radiopaque markers 122, 123 on the dilator 108 and sheath tip 124 come to overlap in the RA 206 confirming that the outer diameters of both catheters are equivalent and ready to be advanced into the LA 208 as a single unit. The sheath tip 124 now comes to rest across the FO 202 and in the LA 208. Again, all the dilator 108 and sheath 100 manipulations are carried out as a single-handed procedure. The dilator 108 is removed, keeping the GW wire loops 24, 26 and sheath 100 stationary in the LA 208.

The elongated proximal segment of the GW 10 is loaded with the primary device that is now advanced to the sheath tip 124 and the GW 10 is removed. The sheath 100 can then be more finely manipulated to deliver the device to the target and subsequently deployed. After deployment, the deflectable sheath 100 is drawn back into the RA 206 and subsequently removed from the patient. The heparin is reversed with protamine and the percutaneous vascular entry is closed.

This transseptal procedure is carried out with a forward-looking catheter system which is iteratively advanced onto a precise position of the FO 202 prior to being punctured. The nature of the catheter system is such that only one device shape will be required to access the LA 208. This is unlike current techniques where catheters are torqued into the FO 202 using a multitude of catheter sizes which may be initially too small and unable to reach the FO 202 or too long placing the patient at risk for slipping off the FO membrane and potentially perforating the RA free wall.

Guidewire, Needle, Dilator and Sheath

Figure 9A:
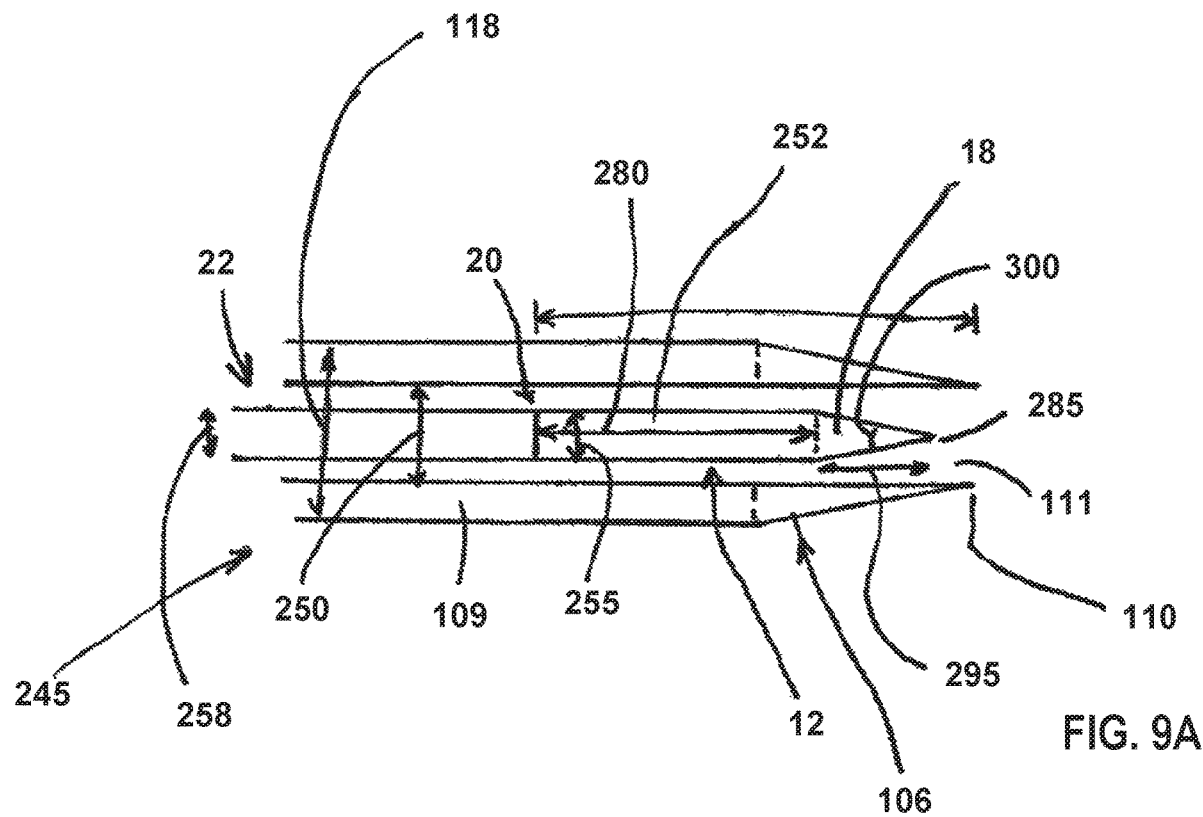
FIG. 9A is a sectional view of a dilator distal region and having a guidewire distal end and needle contained within the dilator lumen.
Figure 9B:
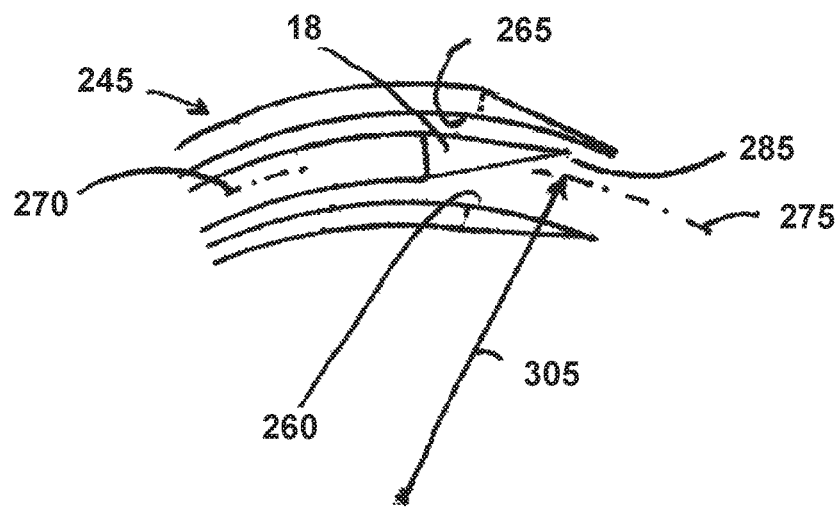
FIG. 9B is a sectional view of a dilator distal region extending around a radius of curvature with a needle body and needle tip contained with the dilator lumen.

FIGS. 9A and 9B show an embodiment for the guidewire distal end 22, which can be the distal end of guidewire loop 14 of the transseptal guidewire 10 of the present subject matter, as described earlier in FIGS. 1-4. The transseptal guidewire 10 can be positioned within the dilator distal segment 106 of the dilator shaft 109 of the present subject matter. The dilator shaft 109 and dilator distal segment 106 have a dilator lumen 111 with a dilator lumen diameter 250 that allows ease of passage of the guidewire needle tip 18, guidewire loop segment 14, and transseptal needle 12 therethrough without significant frictional forces. As shown in FIGS. 9A and 9B, the needle body 252 with a needle body diameter 255, which is shown to be the same diameter as the guidewire diameter 258, can be smaller than the dilator lumen diameter 250 by about 0.002 in, for example (range 0.001-0.004 in, inclusive). The needle body diameter 255 is not significantly smaller than the dilator lumen diameter 250 such that the dilator inner curve wall 260 and dilator outer curve wall 265 can make contact with the needle body 252 and provide alignment of the needle body central axis 270 with the dilator central axis 275. The needle 12 can have a needle length of about 5 mm (range 3-20 mm, inclusive) to provide axial alignment of the needle body 252 that is coaxial with the dilator central axis 275.

Figure 14A:
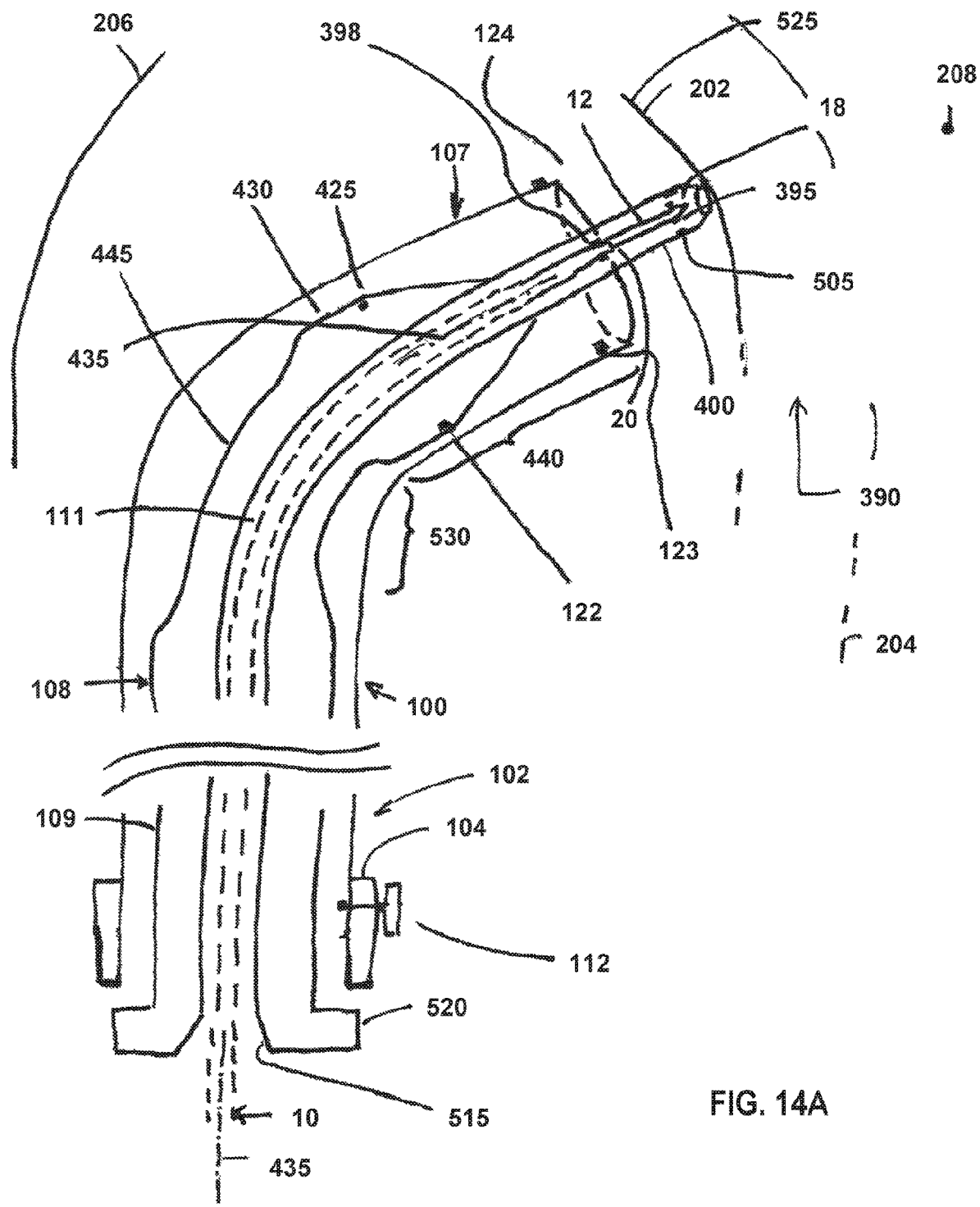
FIG. 14A is a sectional view of a transseptal guidewire located within a dilator which is located within a deflectable sheath, the dilator nose forming a tenting of the FO.

The needle tip 18 can extend with a conical or tapered shape from the needle body 252 forming a sharp needle point 285 that is able to penetrate through tissues found in the FO 202 of the atrial septum 204, as shown in FIG. 14A, or can be used to penetrate other locations peripheral to the FO or penetrate through other vascular walls or an organ septum. To allow the needle-guidewire 10 to traverse in a distal direction within the dilator lumen 111 without making penetrating contact of the needle point 285 with the dilator outer curve wall 265, the needle tip 18 can be formed with a specified needle tip length 295 and needle tip angle 300. As shown in FIG. 9B, the dilator 108 can be bent into a curved shape with a dilator radius of curvature 305. A lower limit for the dilator radius of curvature 305 necessary to access the FO 202 from the inferior vena cava 215 (see FIG. 8) can be about 1 cm (range 0.75-2 cm, inclusive). The dilator lumen diameter 250 can be about 0.035 in, for example (range 0.026-0.038 in, inclusive); the needle body diameter 255 can be about 0.030 in, for example (range 0.025-0.031 M, inclusive). Using standard geometric considerations for a dilator 108 extending around a dilator radius of curvature 305 bend of 1 cm, for example, it can be shown that a needle tip 18 having a needle tip length 295 of approximately 2 mm and a needle tip angle of 26 degrees, for example (range 8-30 degrees, inclusive) will provide for travel of the needle tip 18 around the dilator radius of curvature 305 without allowing the needle point 285 to stick or penetrate into the dilator outer curve wall 265. Various needle tip 18 shapes (such as nonlinear surface curvature) and angles can be used to alter the needle tip length 295 and needle tip angle 300. A close tolerance between the needle body diameter 255 of about 0.002 in, for example, smaller than the dilator lumen diameter 250 will provide for axial alignment of the needle body 252 and needle tip 18 such that buckling of the needle 12 at the hinge point 20 is not significant and the transseptal dilator 108 will direct the needle 12 in coaxial alignment with the dilator central axis 275.

FIGS. 10A-10D show embodiments for the hinge point 20 located between the guidewire distal end 22 and the needle body 252. The hinge point 20 or hinge 20 can be formed from an elastic material such as stainless steel, Nitinol, or other elastic metal, for example, which has a specified equilibrium shape such as a 90 degree bend, or preferably a more acute bend, for example. If the hinge point 20 is temporarily straightened out into a linear configuration due to a constraining force such as that provided by a dilator 108, for example, the hinge 20 will return to its bent shape upon removal of the constraining force. The hinge point 20 or hinge 20 can be formed as a contiguous portion of the guidewire distal end 22 that is joined to the needle body 252, the hinge 20 can be a contiguous portion of the needle body 252 that is joined to the guidewire distal end 22, or the hinge 20 can be a separate region that is joined to both the needle body 252 and joined to the guidewire distal end 22. The hinge 20 can be formed from Nitinol, for example, that is contiguous with a Nitinol needle; the needle 12 can be joined or attached to the guidewire distal end 22. The joining process can include various welding, brazing, or soldering methods or can use adhesives or mechanical joining methods. Alternately, thermal processing methods can be used to form the hinge point 20 into an equilibrium shape that has a specific abrupt angle such as an acute angle, for example.

Figure 10A:
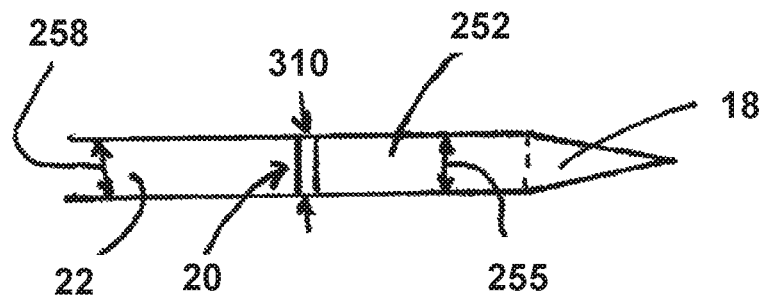
FIG. 10A is a side view of a guidewire distal end and needle with a hinge point located therebetween.
Figure 10B:
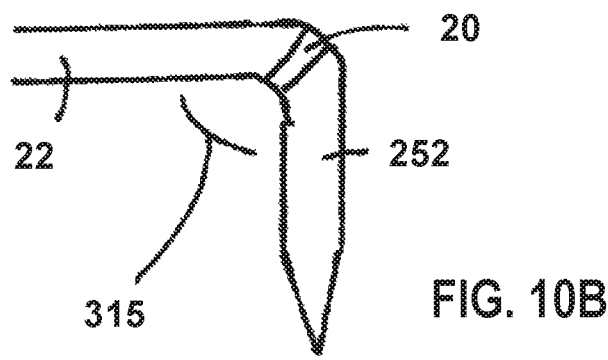
FIG. 10B is a side view of a guidewire distal end forming a needle-guidewire angle with a needle body.

The hinge point 20 can be formed from a hinge 20 that is cylindrical in cross-section and having a hinge diameter 310 that is equal to that of the guidewire diameter 258 or the needle body diameter 255, as shown in FIG. 10A. The hinge 20 can be formed from an elastic material such as Nitinol or Elgiloy, for example, such that it maintains a generally linear shape while contained within the dilator lumen 111 but bends upon delivery of the hinge 20 out of the dilator distal tip 110 or dilator distal end 110 forming an equilibrium shape having, for example, an acute needle-GW angle 315 or bend (range 45-140 degrees, inclusive) between the guidewire distal end 22 and the needle body 252, as shown in FIG. 10B.

Figure 10C:
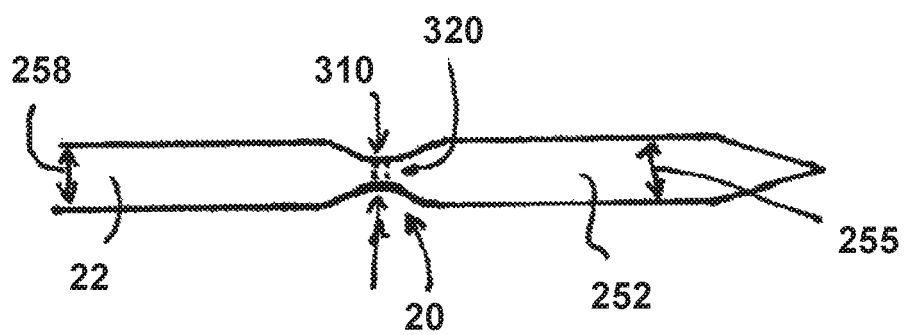
FIG. 10C is a side view of a smaller diameter cylindrical hinge point located between a larger diameter guidewire distal end and a needle body.

In an alternate embodiment, the hinge point 20 can be formed with a circular hinge cross-section 320 with a hinge diameter 310 smaller than the guidewire diameter 258 or the needle body diameter 255, as shown in FIG. 10C. The smaller hinge diameter 310 allows the hinge 20 to bend via elastic deformation of Nitinol material, for example, as it travels within the dilator lumen 111 in a generally linear configuration. Upon release of the hinge 20 from the dilator distal tip 110, the needle body 252 forms a specified needle-GW angle 315 (range 45-140 degrees, inclusive) with the guidewire distal end 22.

Figure 10D:
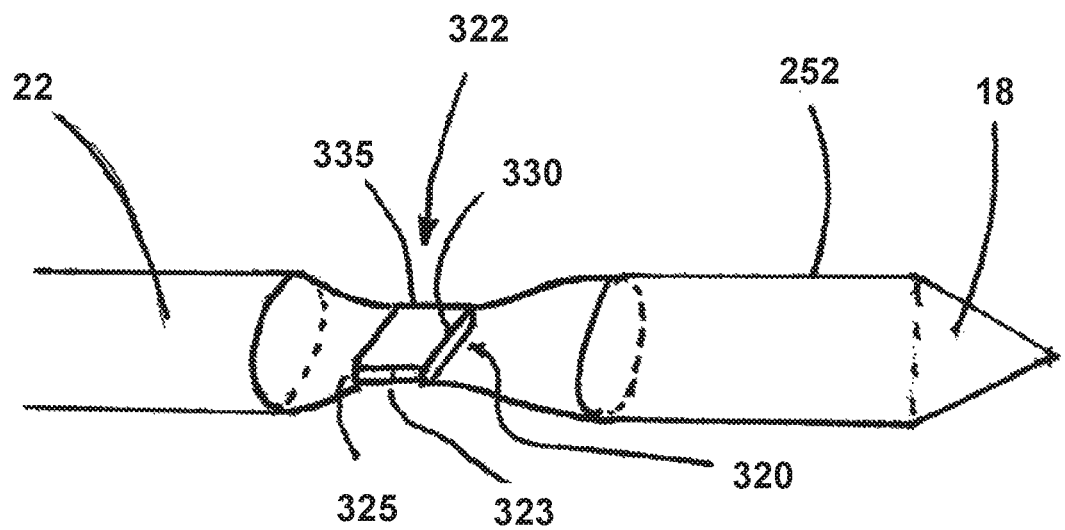
FIG. 10D is a side view of a rectangular hinge point located between a cylindrical guidewire distal end and a needle body.
Figure 10E:
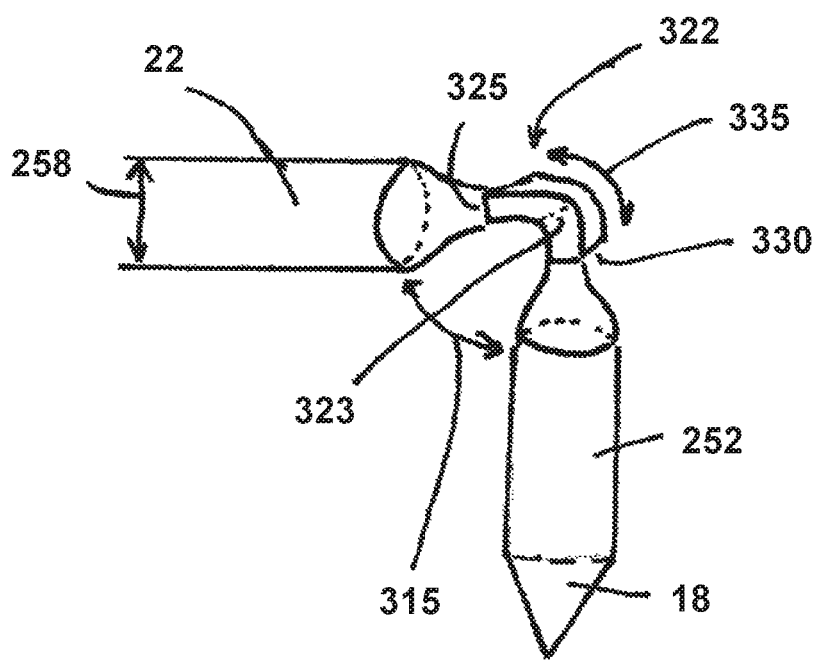
FIG. 10E is a side view of a rectangular hinge point bent to a needle-guidewire angle along a hinge bending axis.

In still another embodiment, the hinge point 20 can be formed with a rectangular hinge 322 with a hinge cross-section 320, as shown in FIGS. 10D and 10E. The hinge 20 can again be formed from an elastic material but has been machined or otherwise formed to a rectangular shape that can provide benefits over a circular shape. Since the needle body 252 is intended to bend in a specific direction defined by the plane of the guidewire loop segment 14 (as shown as loop segments 14 generally in the plane of the paper, for example), the hinge 20 can be formed such that the hinge bending axis 323 is coplanar with the loop segment 14. The hinge height 325 can be much smaller than the hinge width 330, thereby allowing for ease of bending the hinge 20 while maintaining the hinge 20 well below its elastic limit such that the bending remains completely elastic while confined within the dilator lumen 111. The hinge width 330 can be equal to the guidewire diameter 258 at the guidewire distal end 22 and can have a rounded edge that is similar in curvature to the curvature of the guidewire distal end 22; the hinge width 330 being larger than the hinge height 325 can provide optimal push of the guidewire 10 being transferred to the needle body 252 such that the needle tip 18 can be pushed across the FO 202, as shown in FIG. 14A. The hinge length 335 can be adjusted to ensure that the hinge 20 remains in an elastic state during its generally linear configuration within the dilator 108 such that upon release of the hinge 20 from the dilator distal tip 110, the hinge 20 will bend to an acute needle-guidewire angle 315, for example, (range 45-140 degrees) thereby bending the needle body 252 acutely relative to the guidewire distal end 22, as shown in FIG. 10E.

A longer hinge length 335 spreads the bending deformation over the longer length and hence the hinge point 20 retains greater elasticity for returning to an equilibrium bent shape after being delivered within the dilator 108 in a straightened shape. The hinge height 325, which can be smaller than the guidewire diameter 258, further maintains the hinge point 20 in an elastic condition during flexion of the hinge point 20. The hinge height 325 along with the hinge width 330 determine the amount of force provided to fold the needle to an acute angle with respect to the guidewire distal end 22 upon exiting the transseptal dilator 108. The hinge 20 can thereby be designed with a smaller hinge height 325, for example, relative to the guidewire diameter 258 to provide a smaller bending force to fold the needle body 252 than forming a hinge 20 from a cylindrical wire with the hinge 20 having the same diameter as the guidewire diameter 258.

Figure 11A:
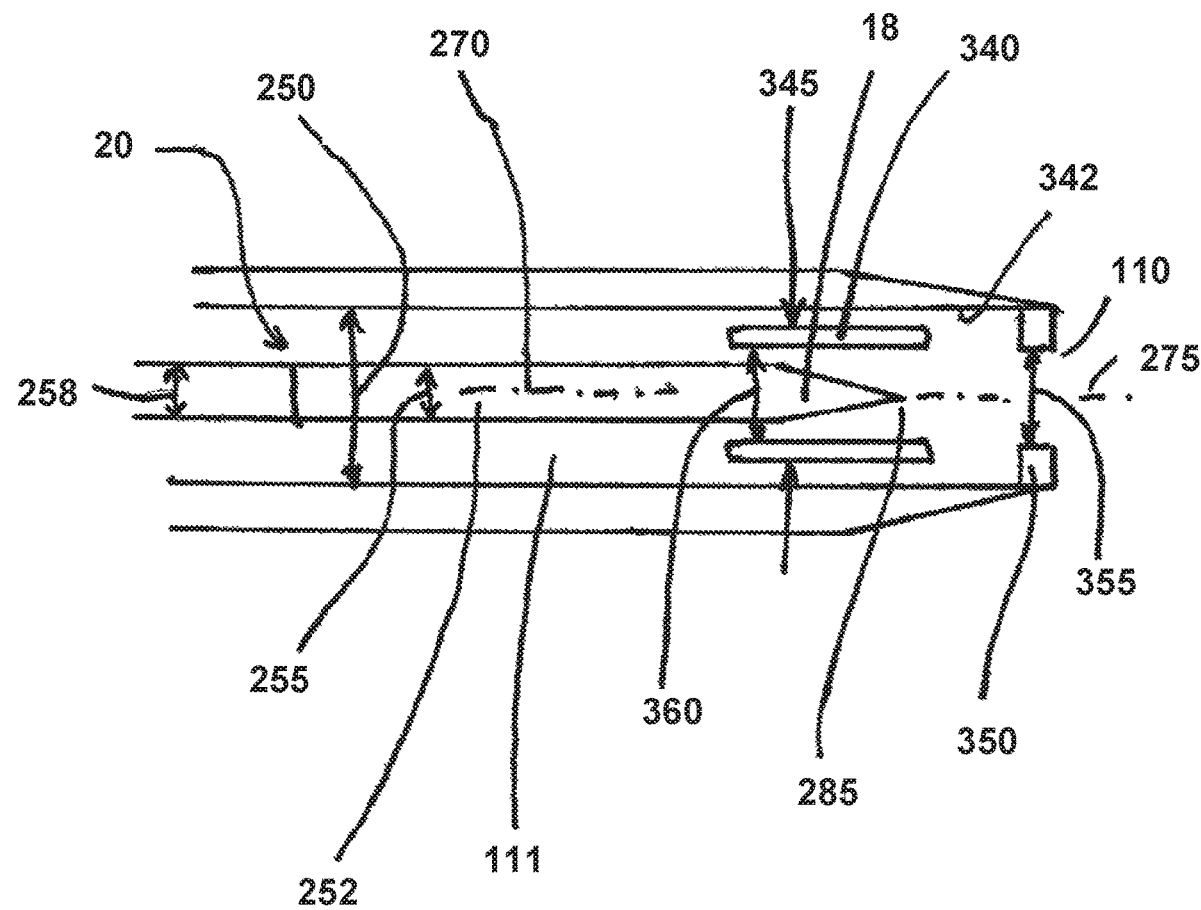
FIG. 11A is a sectional view of a dilator distal region with a guidewire needle surrounded by a tip sheath contained within the dilator lumen.
Figure 11B:
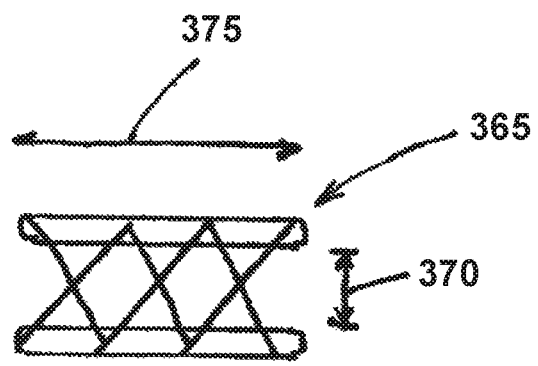
FIG. 11B is a side view of a releasable tip sheath.
Figure 11C:
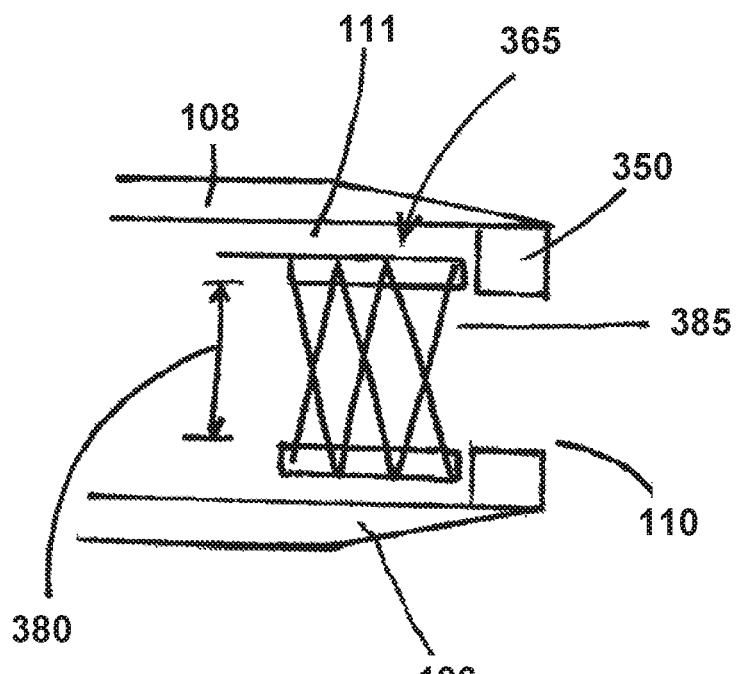
FIG. 11C is a sectional view of a releasable tip sheath contained within the dilator lumen.

In yet another embodiment, as shown in FIGS. 11A-11C, a tip sheath 340 is placed around the needle tip 18 to provide collinear alignment of the needle body central axis 270 with the dilator central axis 275. As shown in FIG. 11A, a tip sheath 340 is placed around the needle tip 18 and extends slightly distally to the needle point 285. The tip sheath 340 can fit via a frictional fit around the needle body 252 to allow the transseptal guidewire 10 and needle to traverse in a distal direction within the dilator lumen 111 without buckling and without the needle point 285 puncturing into the dilator luminal wall 342. The tip sheath 340 is formed such that it has a tip sheath outer diameter 345 that provides adequate clearance of 0.003 in, for example (tip sheath diameter is 0.002-0.005 in smaller than the dilator lumen diameter 250) from the dilator lumen diameter 250 to allow for ease of movement of the tip sheath 340 and needle body 252 together as they are advanced distally within the dilator lumen 111. Located at the dilator distal tip 110 can be a dilator stop 350 that prevents movement of the tip sheath 340 from inside the dilator lumen 111 to a region outside of the dilator 108. The dilator stop diameter 355 can be 0.004 in, for example (range 0.002-0.008 in, inclusive) less than the tip sheath outer diameter 345 to prevent the tip sheath 340 from exiting the dilator lumen 111 across the dilator stop 350. As the needle body 252 and tip sheath 340 are advanced through the dilator lumen 111 in a distal direction, the tip sheath 340 will make contact with the dilator stop 350 and will remain in contact with the dilator stop 350 while the needle body 252 which can be 0.002 in smaller, for example (range 0.001-0.005 in, inclusive, smaller) than the dilator stop diameter 355 is able to pass freely through the dilator stop 350. The tip sheath 340 can provide the needle tip 18 with a protective covering that prevents the needle tip 18 from puncturing into the dilator luminal wall 342 and can also provide the needle body central axis 270 with collinear alignment with the dilator central axis 275.

The tip sheath 340 can be formed from a lubricious plastic material such as Teflon, for example, such that it can slide well relative to the dilator luminal wall 342 during traversal through the dilator 108. Also, the Teflon surface allows the needle body 252 and transseptal guidewire 10 to pass through the inner surface of the tip sheath 340 after the tip sheath 340 has made contact with the dilator stop 350. The tip sheath inner diameter 360 can be 0.002 in smaller than the guidewire diameter 258, for example, to provide unrestricted movement of the guidewire 10 through the dilator stop 350.

In yet another embodiment, the tip sheath 340 as described in FIG. 11A can be a releasable tip sheath 365 formed such that it provides a release from the needle body 252 after the releasable tip sheath 365 has made contact with the dilator stop 350, as shown in FIGS. 11B and 11C. The releasable tip sheath 365 can be formed such that it has a tip sheath equilibrium inner diameter 370 that is about 0.002 in smaller, for example (range 0.001-0.010 in smaller) than the needle body diameter 255. The smaller tip sheath equilibrium inner diameter 370 can provide a releasable holding attachment of the releasable tip sheath 365 to the needle body 252 during distal traversal of the needle body 252 through the dilator lumen 111. The releasable tip sheath 365 can be formed, for example, with a braided tubular structure or with an elastomeric polymeric tubular structure that tends to enlarge in diameter as it is forced into a shorter tip sheath length 375. Upon contact of the releasable tip sheath 365 with the dilator stop 350, as shown in FIG. 11C, the releasable tip sheath 365 is forced into compression upon contact with the dilator stop 350 and tends to enlarge in diameter to a releasable tip sheath expanded diameter 380 that has a larger releasable tip sheath expanded diameter than the needle body diameter 255; the expansion of the releasable tip sheath 365 thereby allows the needle body 252 and guidewire 10 to pass freely through the releasable tip sheath lumen 385 and out of the dilator tip.

Figure 12:
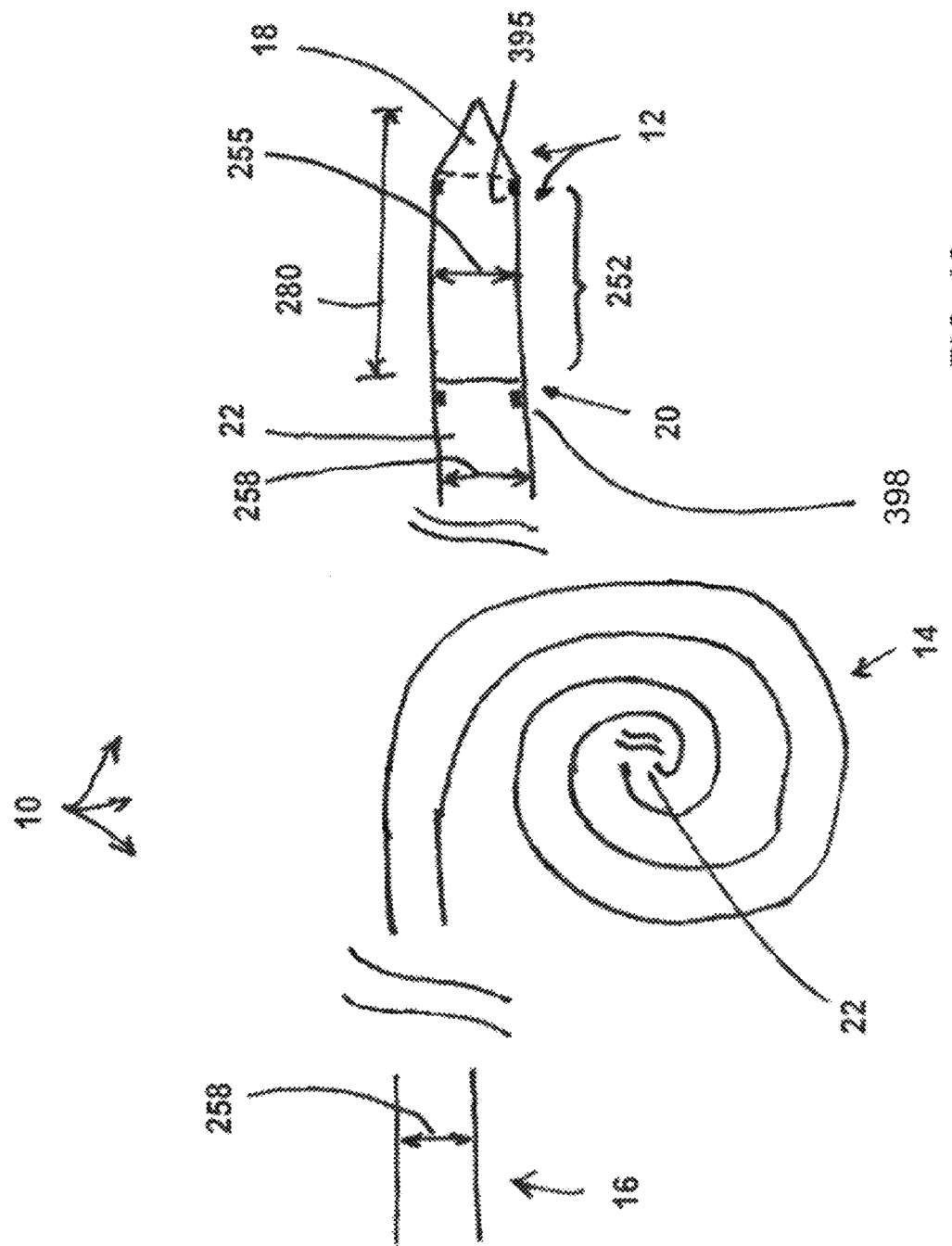
FIG. 12 is a side view of a transseptal guidewire having a proximal guidewire segment, a guidewire loop segment, and a needle.

The transseptal guidewire 10 (needle-guidewire or guidewire), dilator 108, and deflectable sheath 100 of the present subject matter can comprise a structure and configuration as shown in FIGS. 12, 13, and 14A-14F; the present subject matter can be used to cross the FO from the RA into the left atrial chamber, for example, to perform a diagnostic or therapeutic procedure. It is understood that the present subject matter can also be used for crossing the wall of a vascular conduit, crossing another septum of the heart, or crossing a wall/septum of another organ of the body. The guidewire proximal segment 16, guidewire loop segment 14 and guidewire distal end 22 are shown in FIG. 12 and have been described earlier in FIGS. 1-4 and 7-8. The subject matter is intended to provide safe and efficient passage of the needle-guidewire 10 of the present subject matter across a FO wall 390 without allowing the abrupt bending of the transseptal needle from inadvertently impinging or penetrating into the atrial septum 204 and preventing proper formation of the guidewire loop segment 14 in the LA. As shown in FIGS. 12, 13, and 14A-14F, the transseptal guidewire 10 can have a hinge point 20 that allows the needle body 252 to bend abruptly and form a needle-guidewire angle 315, such as an acute angle, for example, (range 45-140 degrees, inclusive) with the guidewire distal end 22. As the needle body 252 extends out of the dilator 108 and into the LA 208

(see FIGS. 14A-14F), it is important that the needle tip 18 does not impinge or penetrate into the atrial septum 204 thereby preventing the loop segment 14 from being delivered properly into the LA 208 as described earlier. To help identify the location of the needle tip 18 when delivering the needle tip 18 across the atrial septum 204, a distal guidewire radiopaque marker 395 can be located on the needle body 252 at a location adjacent to the needle tip 18. A guidewire hinge radiopaque marker 398 may be located on the guidewire distal end 22 adjacent to the hinge 20 to provide fluoroscopic visualization of the needle body position relative to the dilator distal tip as identified via fluoroscopic visualization of the dilator distal radiopaque marker 505. It is noted that external markers can alternately or additionally be placed onto the guidewire proximal segment 16 and dilator shaft 109 at a location outside of the patient's body; such external markers can be used to determine axial positioning of the guidewire needle tip 18 relative to the dilator distal end 110 during tenting of the FO and during advancement of the needle-guidewire 10 and dilator 108 across the FO.

The transseptal guidewire 10, as shown in FIG. 12, can be formed from a metal such as stainless steel, Nitinol, or other materials commonly used to form standard guidewires used in the medical device industry. The needle length 280 can be about 5 mm, for example (range 3-15 mm, inclusive), and is intended to have adequate needle length 280 to cross through the 2-3 mm thick wall 390 of the FO 202 and still have at least 1-2 mm of axial length of the transseptal needle extending within the dilator nose 400 (see FIGS. 13 and 14A) to hold the needle in axial alignment with the dilator nose 400 without bending at the hinge point 20 as will be further described in FIG. 14B and later in this specification. A shorter needle length 280 (still within the needle length range) could require multiple short advancements (e.g., 2-3 advancements of 1-3 mm axial movements) of the needle to cross the FO wall 390 followed by multiple similar advancements of the dilator nose 400 which provided the axial alignment support for the needle. A longer needle length 280 (still within the needle length range) would require a longer dilator nose length 415 (see FIGS. 13 and 14A-14D) to ensure that the needle did not penetrate into the atrial septum 204 following exiting of needle from the dilator distal end 110 and bending of the needle-guidewire 10 at the hinge point 20; such a longer needle length 280 may also result in impingement of the needle tip 18 into the LA lateral wall 405 (see FIG. 14C) during deployment of the needle tip 18 from the dilator distal tip 110 or dilator distal end 110. The needle length 280 and dilator nose length 415 used in the present subject matter are intended to deliver the needle 12 into the central region of the LA prior to delivery of the full needle-guidewire 10 into the LA.

Figure 13:
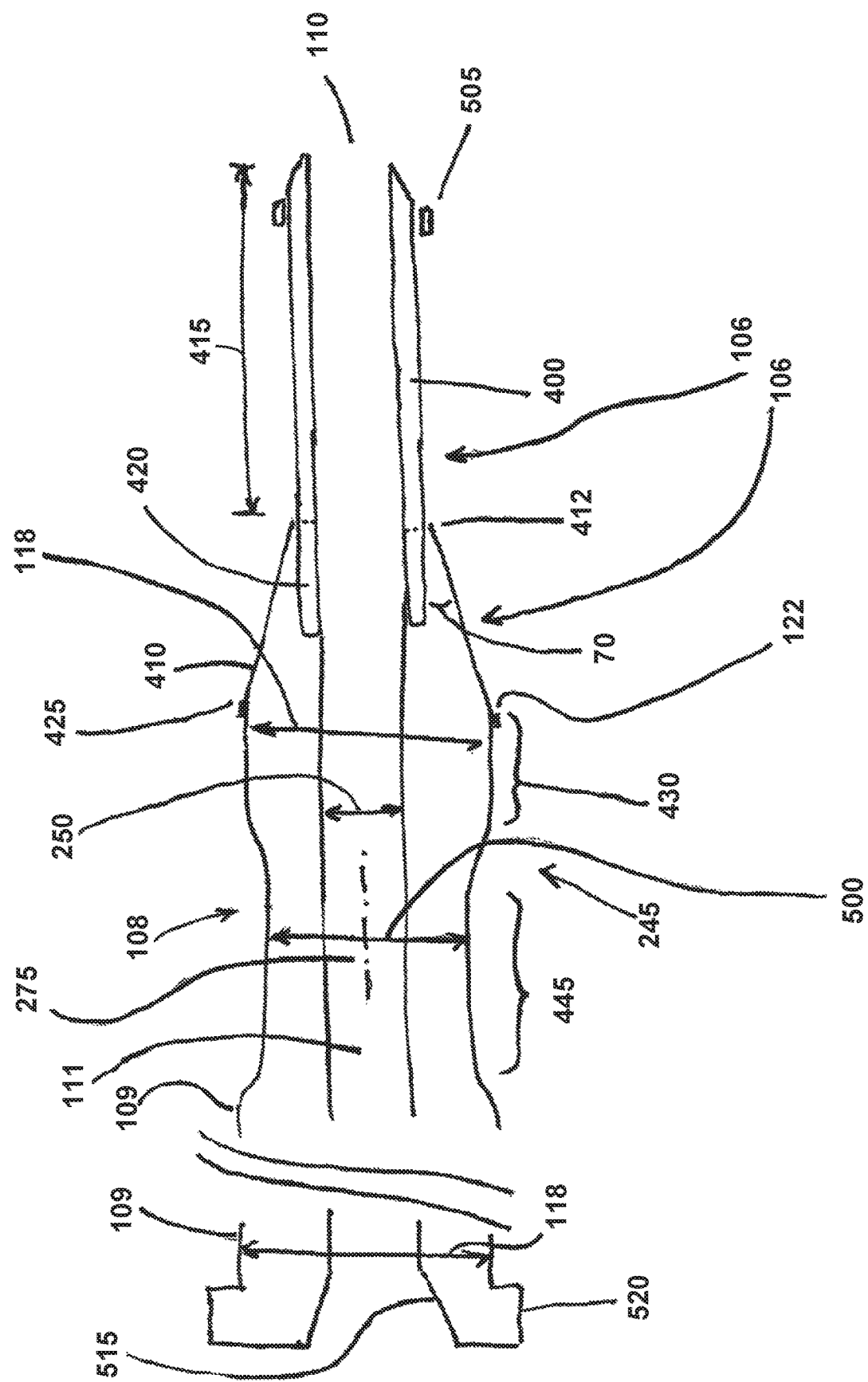
FIG. 13 is a sectional view of dilator having a dilator nose, a dilator alignment zone, a dilator waist, and a dilator lumen that extends to a dilator proximal port located on a dilator manifold.

The dilator distal region 245 of an embodiment of the present subject matter, as shown in FIGS. 13 and 14A, can have a dilator distal segment 106 that comprises a dilator beveled segment 410 and a dilator nose 400. The outer cylindrical surface of the dilator nose 400 contacts the outer surface of the beveled segment 410 at a dilator inflection point 412. The dilator nose 400 extends from the beveled segment 410 to the dilator distal tip 110 and has a thin-walled cylindrical shape that is easily extended through the FO wall 390 without significantly dilating the FO 202 FO due to the low profile thin-walled dilator nose 400. The dilator nose 400 is thereby able to direct the needle of the transseptal guidewire 10 through the FO and into the chamber of the LA 208 without allowing the needle to bend abruptly and potentially impinge or penetrate into the atrial septum 204. The dilator nose length 415 can be 9 mm, for example, (range 5-18 mm); a shorter dilator nose length 415 may not direct the needle across the FO wall 390 into the LA 208 thereby allowing hinge point 20 of the needle to bend to an acute angle and potentially impinge or penetrate into the atrial septum 204. A longer dilator nose length 415 may not provide the support to direct the needle perpendicular to the plane of the FO; additionally such a longer nose length 415 may extend further into the LA 208 than desired thereby potentially directing the needle tip 18 to be delivered into the LA 208 and impinging upon the lateral wall 405 of the LA 208 (see FIG. 4C).

The dilator nose 400 can be formed from a thin-walled hypo tube made of stainless steel, Nitinol, or other metal or it can be formed from a polymeric material such as polyimide, polyethylene terephthalate, or other polymer that is high in tensile strength and can be formed into a thin-walled (e.g., wall thickness of 0.003 in, range 0.0015-0.005 in, inclusive) tube with a dilator lumen diameter 250 able to provide passage with close tolerance (e.g., 0.002-0.004 in, inclusive, clearance) for a 0.035 in (range 0.025-0.038 in, inclusive) transseptal guidewire 10 or standard guidewire. Thus the dilator nose 400 has an outer diameter that is similar to the guidewire fixed diameter 258 to provide the dilator nose 400 with easy transitional access across the FO 202. The dilator nose 400 can extend within and can be permanently attached to the dilator beveled segment 410 via adhesives, insert molding into the polymeric material of the dilator 108, thermal bonding, solvent bonding, or other bonding methods. The dilator beveled segment 410 provides support and a stable foundation to a nose support region 420 of the thin-walled tube that forms the dilator nose 400, as shown in FIG. 13. The dilator beveled segment 410 extends proximally from the dilator nose 400 in a tapered manner from a small diameter equal to the diameter of the dilator nose 400 to a dilator shoulder 425 having a larger diameter equal to the dilator fixed diameter 118 that is able to pass with minimal friction within and with full side support from the deflectable sheath 100 (sheath diameter is about 8.5 Fr, range 6 Fr to over 20 Fr, for example) as described earlier. The dilator beveled segment 410 can be formed of the same material as and contiguously with the dilator nose 400 by forming these portions of the dilator with a material that is suitable to the functional aspects of the lubricious dilator bevel segment 410 and the thin-walled high compressive strength dilator nose 400 that can be advanced over a guidewire without collapse.

The dilator 108 can have a cylindrically shaped dilator alignment zone 430 having the dilator fixed diameter 118 extending proximally from the dilator shoulder 425 for an axial distance of 5 mm (range 3 mm to the full dilator shaft 109 proximal to the dilator shoulder). The dilator alignment zone 430 provides for axial alignment of the dilator central axis 275 with the sheath central axis 435 in the sheath straight region 440, as shown in FIG. 14A. The purpose of the dilator axial alignment zone 430 is to provide controlled directionality to the dilator axial alignment zone 430 and the dilator nose 400 such that the dilator alignment zone 430 and the dilator nose 400 are directed via the deflectable sheath 100 to be perpendicular to the FO during tenting 525 and prior to penetrating the FO 202 with the needle-guidewire 10. The axial alignment zone 430 enhances the ability of the needle to retain the desired target site within the FO 202 without sliding along the surface of the FO resulting in an angled septal puncture.

The transseptal dilator 108 of the present subject matter can have a dilator waist 445 located proximal to the dilator alignment zone 430 and extending for about 20 mm (range 5-50 mm, inclusive) to extend throughout the axial length of the sheath bend region 530 (see FIG. 14A). The dilator waist 445 provides a region of the dilator shaft 109 that is more flexible than the remainder of the dilator shaft 109 proximal to the dilator shoulder 425 but still with adequate pushability or dilator shaft 109 compression characteristics. The dilator waist 445 can have a dilator waist diameter 500, for example, which is 50 percent (range 30-95 percent, inclusive) of the diameter of the dilator fixed diameter 118. The waist 445 can also be formed from a polymer that has a lower durometer polymer, for example, than the remainder of the dilator shaft 109 such that the dilator waist diameter 500 can be uniform and equal to the dilator fixed diameter 118 but has a greater flexibility and retains adequate pushability.

A radiopaque marker such as a dilator distal radiopaque marker 505 is placed near the dilator distal tip 110. The distal dilator radiopaque RO marker 505 allows the physician to visualize the location of the dilator distal tip 110 relative to the distal guidewire RO marker 395 to ensure that the needle tip 18 is not protruding from the dilator distal tip 110 as the dilator distal tip 110 is being positioned against the FO to form a tenting 525 of the FO as described earlier.

A dilator shoulder radiopaque marker 122 is located on the dilator shoulder 425 adjacent to the dilator beveled segment 410. The dilator shoulder radiopaque marker 122 can be aligned or overlapped (under fluoroscopy) with the distal sheath radiopaque marker 123 such that they overlap one another in an axial direction for the sheath 100 and dilator 108. Such alignment is used by the physician during delivery of the dilator 108 and sheath 100 over a standard guidewire through the vasculature of the body and into the RA. This alignment is also used by the physician to ensure a smooth transition of the sheath 100 and dilator 108 together with a flush diameter fit over the transseptal guidewire 10 of the present subject matter as the sheath 100 and dilator 108 are advanced together across the FO wall 390.

A dilator proximal port 515 located on the dilator manifold 520 can be used to provide access for a standard guidewire and also to provide passage for the transseptal guidewire 10 of the present subject matter. It is further noted that the presence of the dilator nose 400 on the distal dilator segment 106 provides an additional benefit for the present transseptal dilator 108 subject matter for the use of the dilator proximal port 515. With the dilator nose 400 positioned across the FO, the transseptal guidewire 10 can be removed from the dilator 108 and the dilator lumen 111 can be used to provide pressure measurement within the LA 208. The dilator proximal port 515 can be attached via appropriate pressure transduction tubing to a pressure transducer located outside of the patient's body in order to acquire a pressure reading in the LA 208 either prior to or following a therapeutic procedure. The transseptal guidewire 10 of the present subject matter can be effectively reintroduced back into the dilator lumen 111 of the present subject matter as needed to complete or resume the therapeutic procedure without need for a guidewire exchange; retracting the needle-guidewire 10 into the introducer would permit easy reintroduction of the needle-guidewire 10.

The transseptal guidewire 10 and dilator 108 of the present subject matter are shown in FIG. 14A contained within the sheath distal segment 107 of the deflectable sheath 100 that is located within the RA 206 and in position to provide tenting 525 by the dilator nose 400 onto the FO 202. As described earlier, the dilator 108 and deflectable sheath 100 had been delivered to the site of the RA 206 over a standard guidewire, and the standard guidewire had been replaced by the transseptal guidewire of the present subject matter. The delectable sheath 100 is initially steered adjacent to the FO using ultrasound or other imaging modalities. FIGS. 14A-14F describe an embodiment for the sequential methods of use for placing the transseptal guidewire 10 across the FO and into the LA.

As shown in FIG. 14A, adjacent to the sheath proximal end 102, the sheath handle 104 has been activated to form a bend in the sheath bend region 530 to align the sheath straight region 440 perpendicular to the plane of the FO 202. The actuator 212 located on the sheath handle 104 can be used to advance the dilator distally or withdraw the dilator proximally in a controlled manner relative to the deflectable sheath 100. The sheath distal end 124 is positioned via ultrasound observation of the distal sheath radiopaque marker 123 such that the sheath distal end 124 is about 5 mm from the FO 202. The needle tip 18 has been withdrawn into the dilator nose 400 during tenting 525 as observed via fluoroscopy that shows the distal GW radiopaque marker 395 being overlapped (or slightly proximal in an axial direction) with the dilator distal radiopaque marker 505 to ensure that the needle tip 18 does not protrude out of the dilator distal end or dilator distal tip 110. The dilator alignment region is in full sliding and supportive contact with the sheath straight region 440 such that the dilator central axis 275 in the region of the dilator nose 400 is coaxial with the sheath central axis 435 in the region of the sheath straight region 440.

The dilator alignment region is held firmly by the sheath straight region 440 such that the deflectable sheath 100 can direct the dilator nose 400 perpendicular to the FO, as shown in FIG. 14A. The dilator waist 445 is located within the sheath bent region such that the enhanced flexibility of the dilator waist 445 does not tend to straighten the sheath bend region 530 during advancement of the dilator 108 within the sheath 100. The flexible dilator waist 445 reduces the tendency for the dilator 108 to form a straight axial configuration throughout its axial length, but rather is able to be easily held in a curved configuration that matches the bend of the sheath bend region 530 and provides perpendicular alignment of the dilator alignment zone 430 and dilator nose 400 perpendicular to the plane of the plane of the FO 202.

Figure 14B:
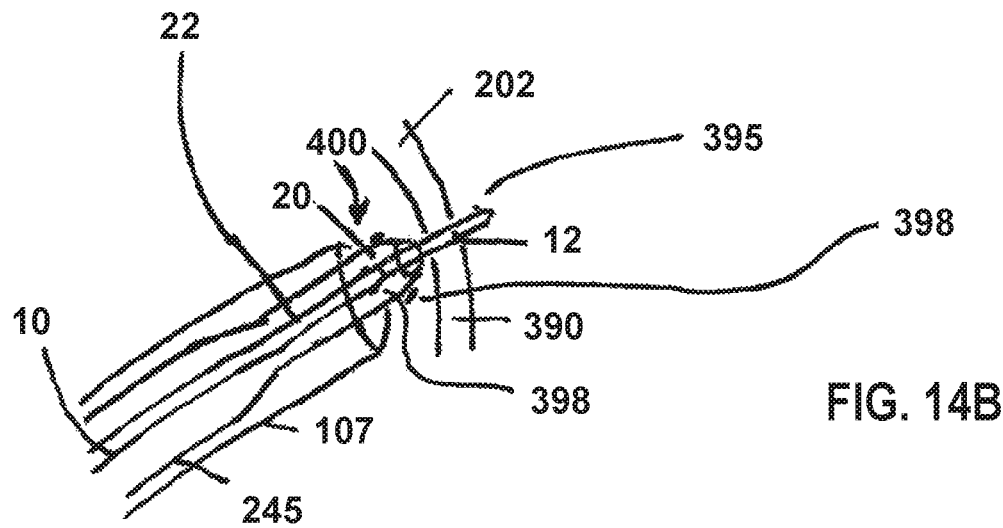
FIG. 14B is a sectional view of a needle partially contained within a dilator nose and extending across the FO wall.
Figure 14C:
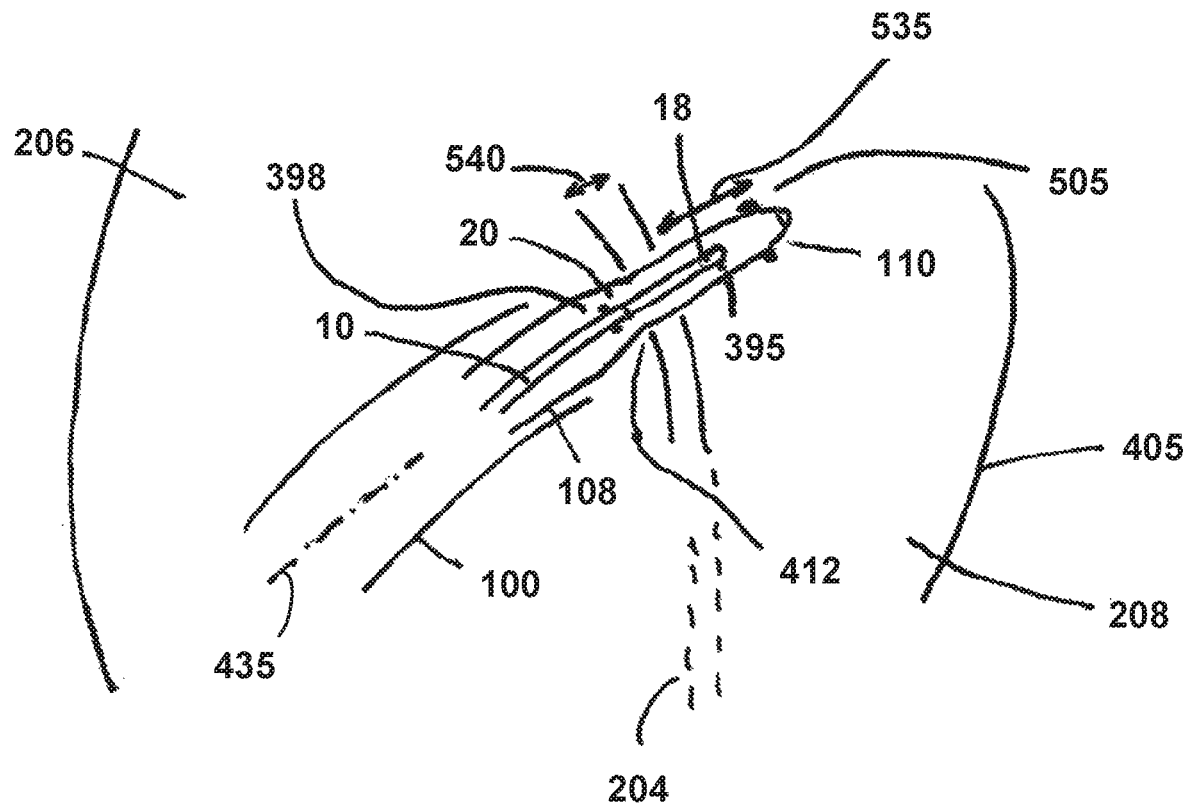
FIG. 14C is a sectional view of a dilator nose being advanced across the FO wall while a guidewire and needle remain fixed in position within a deflectable sheath.

Once confirmed that tenting 525 has occurred in the proper location in the FO 202, the needle can be advanced across the FO wall 390, as shown in FIG. 14B. A portion of the needle distal to the hinge point 20 is contained within the dilator nose 400 to provide axial alignment of the needle body central axis 270 with the dilator central axis 275 in the region of the nose 400 such that the needle body 252 is directed perpendicular to the plane of the FO 202 preventing an angulated puncture of the needle and thus providing resistance to needle advancement across the FO 202. The guidewire hinge radiopaque marker 398 can be observed under fluoroscopy to be positioned proximal to the dilator distal radiopaque marker 505.

With the needle tip 18 advanced across the FO wall 390 (see FIG. 14C) the dilator 108 can be advanced over the transseptal guidewire 10 while maintaining the transseptal guidewire 10 in a fixed position. The dilator distal tip 110 extends distal to the needle tip 18 as evidenced under ultrasound and fluoroscopy by the locations of the dilator distal radiopaque RO marker being distal to the distal guidewire RO marker 395 and extending past the FO wall 390 by a nose penetration distance 535 equal to or greater than the needle length 280. For a FO wall thickness 540 of 3 mm, a 9 mm dilator nose 400, for example, can be advanced over the transseptal guidewire until the dilator inflection point 412 comes into initial contact with the FO thereby providing a nose penetration or protrusion distance 535 of 6 mm into the LA, for example, to ensure that the needle of 5 mm needle length, for example, cannot inadvertently bend at the hinge point 20 and impinge or penetrate into the atrial septum 204.

Figure 14D:
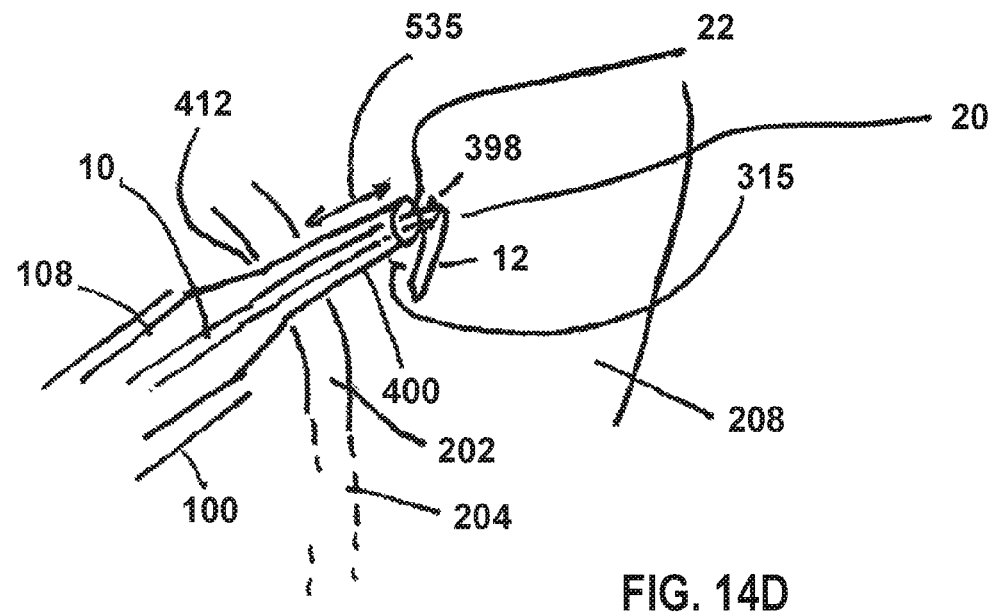
FIG. 14D is a sectional view of a needle being advanced across the FO wall and a guidewire-needle bend angle occurring at a hinge point.

As shown in FIG. 14D the needle-guidewire 10 is advanced through the dilator nose 400 placing the needle into the central region of the chamber of the LA 208 and allowing full deployment of the needle, and allowing the hinge to bend forming an acute needle-guidewire angle 315 with the guidewire distal end 22, preferably between 50-80 degrees, but having a range of 45-140 degrees. The nose protrusion distance 535 into the LA 208 being equal or larger than the needle length prevents the needle from impinging upon or penetrating into the atrial septum 204. The guidewire hinge radiopaque marker 398 has been advanced to a position distal to the dilator distal radiopaque marker 505 as evidenced under fluoroscopy and indicates that the needle 12 extends distal to the dilator distal tip 110.

Figure 14E:
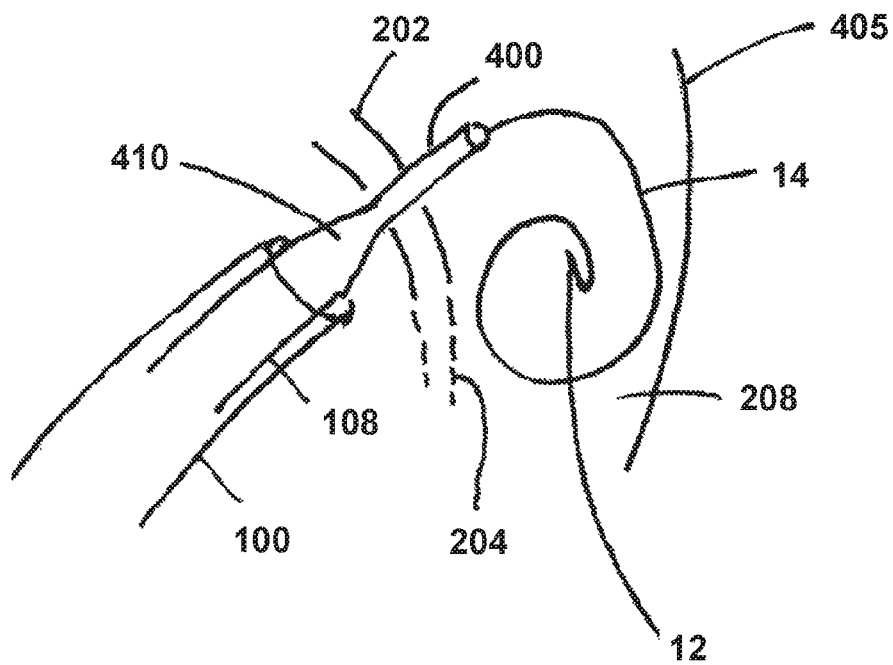
FIG. 14E is a sectional view of a guidewire being advanced further across the FO wall and forming a guidewire loop segment within the LA.

The transseptal guidewire 10 can be further advanced distally within the dilator lumen 111 such that a loop segment 14 is formed in the LA 208, as shown in FIG. 14E. The loop segment 14 can be comprised of multiple loops of different sizes and configurations as described earlier and have an external-most diameter of about 30 mm, range 25-40 mm. The loop segment 14 can make contact with the LA 208 lateral wall 405 and with the atrial septum 204 contributing to guidewire positional stability. The presence of guidewire loop segment 14 within the LA provides the positional stability to advance the dilator beveled segment 410 and deflectable sheath 100 over the needle-guidewire 10 and across the FO 202.

Figure 14F:
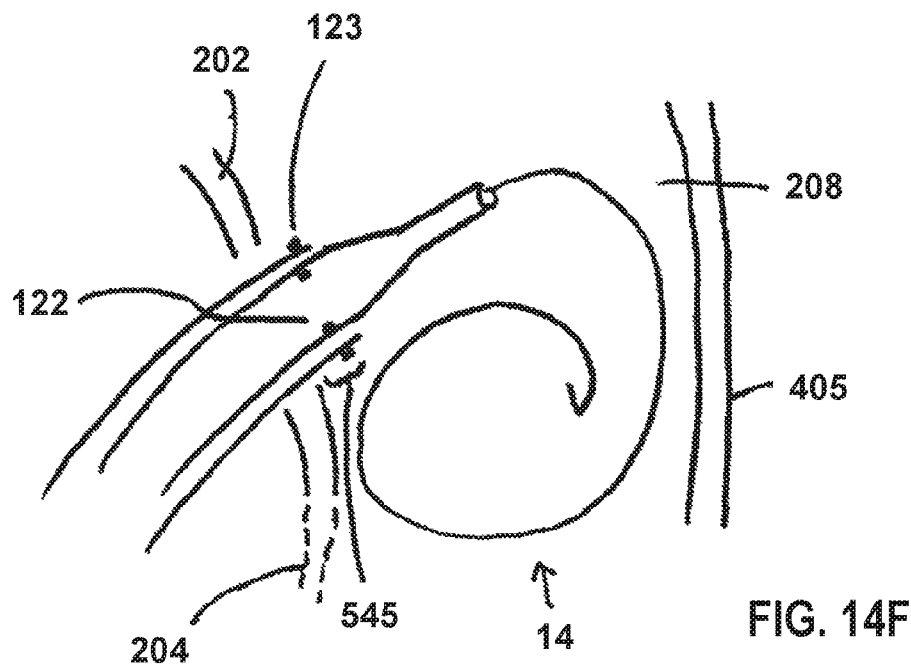
FIG. 14F is a sectional view of a deflectable sheath and dilator being advanced over a transseptal guidewire to place a portion of a sheath into the LA.

The sheath distal end 124 is aligned with the dilator shoulder 425 as evidenced by overlapping of the distal sheath RO marker 123 with the dilator shoulder RO marker 122, as shown in FIG. 14F. The dilator 108 and deflectable sheath 100 are then advanced together across the FO as shown in FIG. 14F placing a sheath protrusion distance 545 of at about 3 mm into the LA, for example.

The deflectable sheath 100 can then be used, following removal of the dilator 108 from the sheath 100, for delivery of diagnostic or therapeutic devices across the FO 202 and over the transseptal guidewire 10. Alternately, the deflectable sheath 100 and dilator 108 can both be removed leaving the transseptal guidewire 10 across the FO for delivery of a diagnostic or therapeutic device across the FO.

Figure 15:
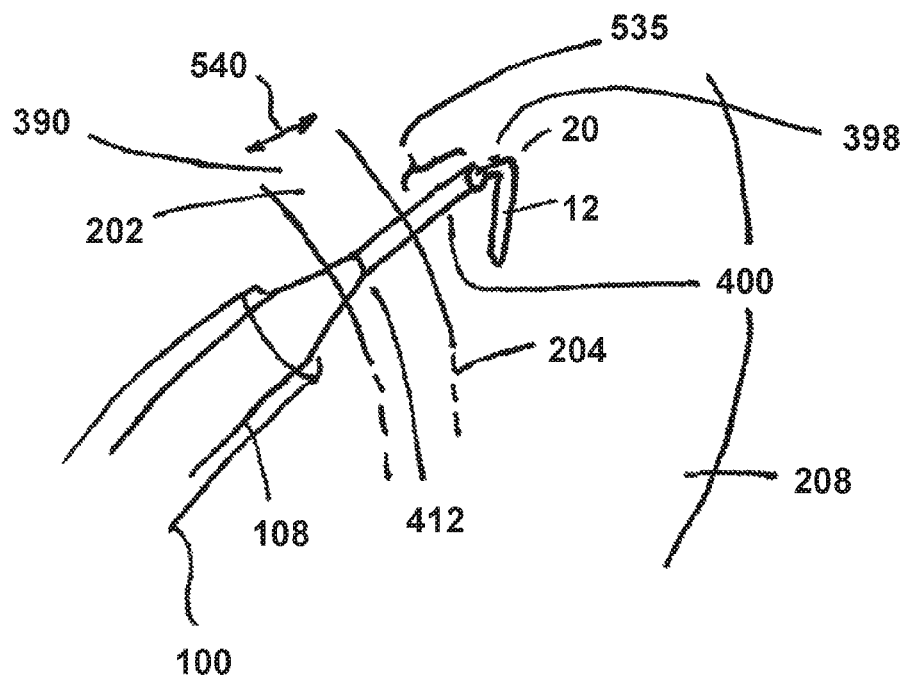
FIG. 15 is a sectional view of an advancement method for small advancement of a guidewire followed by small advancement of the dilator to cross a thickened FO.

As shown in FIG. 15 the FO wall thickness 540 can, upon occasion, be greater than 2-3 mm for some patients, reaching 5 mm or greater FO wall thickness 540 and thereby alter the step shown in FIG. 14D of the methods of use for advancing the transseptal guidewire 10 across the FO. Under the situation of excessively thickened FO wall 390, the physician may desire to advance the dilator inflection point 412 into a portion of the FO wall 390 thereby increasing the amount of dilator nose protrusion distance 535 extending into the LA. The increase in dilator nose protrusion length allows a needle having a needle length that is equal to or less than the nose protrusion length to be safely advanced into the LA 208 without concern that the needle tip 18 could inadvertently impinge or penetrate into the atrial septum 204. Multiple advancement steps of a few millimeters can be performed by advancing the transseptal guidewire 10 followed by advancing the dilator 108 until the FO wall 390 has been successfully traversed and the guidewire loop segment 14 has been successfully delivered into the LA. The remaining steps of the method of use are the same as described previously.

CLOSING NOTES AND EXAMPLES

The above Detailed Description includes references to the accompanying drawings, which form a part of the Detailed Description. The Detailed Description should be read with reference to the drawings. The drawings show, by way of illustration, specific embodiments in which the present subject matter can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the Detailed Description. The scope of use of the examples can be expanded for other uses, e.g., non-transseptal procedures, both vascular and nonvascular cavity organ structures. Also, various features or components have been grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a method of treating a patient can include advancing a dilator located in a lumen of a sheath distally relative to the sheath, including applying a tenting force to a septal wall associated with the fossa ovalis of a heart using a dilator nose located at a distal end portion of the dilator; advancing a tip of a needle attached to a guidewire and located in a lumen of the dilator distally relative to the dilator, including puncturing across the septal wall associated with the fossa ovalis; advancing the dilator distally over the guidewire while maintaining the guidewire and the sheath in a fixed position, including extending a distal end of the dilator nose beyond the septal wall associated with the fossa ovalis by a distance equal to or greater than a length of the needle; and advancing the guidewire distally through the dilator nose, including allowing deployment of the needle in a central region of the left atrium of the heart.

In Example 2, the method of Example 1 can optionally be configured such that advancing the dilator distally relative to the sheath includes manipulating an actuator located on or positioned adjacent to a handle of the sheath.

In Example 3, the method of any one of Examples 1 or 2 can optionally be configured such that, when advancing the dilator distally relative to the sheath, the tip of the needle is positioned within the dilator nose.

In Example 4, the method of any one or any combination of Examples 1-3 can optionally be configured such that, when advancing the tip of the needle distally relative to the dilator, a position of a hinge connecting a distal end of the guidewire and a proximal end of the needle is maintained proximal to the distal end of the dilator nose.

In Example 5, the method of Example 4 can optionally be configured such that allowing deployment of the needle in the central region of the left atrium includes allowing the hinge to bend and form an acute angle between the distal end of the guidewire and the proximal end of the needle.

In Example 6, the method of any one of Examples 4 or 5 can optionally be configured such that allowing deployment of the needle in the central region of the left atrium includes visualizing a position of the hinge relative to the distal end of the dilator nose, and confirming that the hinge is positioned distal to the distal end of the dilator nose.

In Example 7, the method of any one or any combination of Examples 1-6 can optionally further comprise maintaining coaxial alignment between the dilator and the sheath through engagement of a dilator alignment region, located proximal of the dilator nose, with a lumen wall of the sheath.

In Example 8, the method of any one or any combination of Examples 1-7 can optionally be configured such that extending the distal end of the dilator nose beyond the septal wall associated with the fossa ovalis by the distance equal to or greater than the length of the needle includes preventing the needle from impinging upon the left size of the atrial septum of the heart.

In Example 9, the method of any one or any combination of Examples 1-8 can optionally be configured such that advancing the guidewire distally through the dilator nose includes allowing a guidewire loop segment to form in the left atrium.

In Example 10, the method of Example 9 can optionally be configured such that allowing the guidewire loop segment to form in the left atrium includes engaging a portion of the guidewire loop segment with a left atrium lateral wall or the left side of the atrial septum.

In Example 11, the method of any one of Examples 9 or 10 can optionally further comprise advancing the dilator and the sheath distally over the guidewire and across the septal wall associated with the fossa ovalis, including extending a dilator bevel segment, located proximal to the dilator nose, into the left atrium followed by a dilator shoulder, located proximal to the dilator bevel segment, and a sheath distal end.

In Example 12, the method of Example 11 can optionally further comprise removing one or both of the dilator and the sheath from the patient and delivering a diagnostic or therapeutic device over the guidewire and across the septal wall associated with the fossa ovalis.

In Example 13, the method of any one or any combination of Examples 1-12 can optionally further comprise, prior to advancing the guidewire distally through the dilator nose, withdrawing the guidewire proximally and using the lumen of the dilator to measure pressure within the left atrium.

In Example 14, an anatomical wall crossing system can comprise a dilator extending from a proximal end portion to a distal end portion and including a lumen therethrough. The distal end portion can include a dilator nose and a dilator beveled segment. The dilator nose can have a first outer diameter and a length of about 5-18 mm, inclusive. The dilator beveled segment can extend proximally of the dilator nose and can taper from a second outer diameter, greater than the first outer diameter, to the first outer diameter.

In Example 15, the wall crossing system of Example 14 can optionally be configured such that the dilator nose includes a cylindrical cross-sectional shape having a wall thickness of about 0.0015-0.005 in, inclusive.

In Example 16, the wall crossing system of Example 15 can optionally be configured such that the dilator nose is formed from a thin-walled hypotube.

In Example 17, the wall crossing system of any one or any combination of Examples 14-16 can optionally be configured such that the dilator further includes a dilator alignment zone extending proximal of the dilator beveled segment and having a substantially uniform outer diameter.

In Example 18, the wall crossing system of Example 17 can optionally be configured such that the dilator further includes a dilator waist extending proximal of the dilator alignment zone and having a greater longitudinal flexibility than the dilator alignment zone.

In Example 19, the wall crossing system of Example 18 can optionally be configured such that the dilator waist has a length of about 5-50 mm, inclusive.

In Example 20, the wall crossing system of any one of Examples 18 or 19 can optionally be configured such that the dilator waist has an outer diameter that is 30-90%, inclusive, of an outer diameter of the dilator alignment zone.

In Example 21, the wall crossing system of any one or any combination of Examples 18-20 can optionally be configured such that the dilator waist is formed from a lower durometer polymer than a polymer of the dilator alignment zone.

In Example 22, the wall crossing system of any one or any combination of Examples 14-21 can optionally further comprise a guidewire deliverable within the lumen of the dilator and extending from a proximal end to a distal end, the distal end attached to a puncture needle having a needle body and a needle tip.

In Example 23, the wall crossing system of Example 22 can optionally be configured such that an intermediate portion of the guidewire includes at least one looped segment.

In Example 24, the wall crossing system of any one of Examples 22 or 23 can optionally be configured such that the puncture needle has a length of 3-20 mm, inclusive.

In Example 25, the wall crossing system of any one or any combination of Examples 22-24 can optionally be configured such that the needle body has a needle body diameter of 0.001-0.004 in, inclusive, less than the lumen of the dilator to facilitate coaxial alignment of a needle body axis and a dilator axis.

In Example 26, the wall crossing system of any one or any combination of Examples 22-25 can optionally be configured such that the distal end of the guidewire is attached to a proximal end of the puncture needle at a hinge.

In Example 27, the wall crossing system of Example 26 can optionally be configured such that the hinge includes a shape memory material and, when unconstrained, forms an angle between the distal end of the guidewire and the proximal end of the puncture needle of 45-140 degrees, inclusive.

In Example 28, the wall crossing system of any one of Examples 26 or 27 can optionally be configured such that the hinge includes a cylindrical cross-sectional shape having a diameter less than a diameter of the guidewire and of the needle body.

In Example 29, the wall crossing system of any one of Examples 26 or 27 can optionally be configured such that the hinge includes a rectangular cross-sectional shape and is configured to bend in a direction defined by a plane of the at least one loop segment.

In Example 30, the wall crossing system of any one or any combination of Examples 22-29 can optionally further comprise a tip sheath placed around the puncture needle to facilitate coaxial alignment of a needle body axis and a dilator axis.

In Example 31, the wall crossing system of Example 30 can optionally be configured such that the dilator includes a dilator stop configured to inhibit distal movement of the tip sheath from a position within the lumen of the dilator to a position external to the lumen of the dilator.

In Example 32, the wall crossing system of Example 31 can optionally be configured such that the tip sheath is configured to expand in diameter as it is placed under compression, thereby allowing its release from the puncture needle upon contact with the dilator stop.

In Example 33, the wall crossing system of any one or any combination of Examples 14-32 can optionally further comprise a deflectable sheath.

In Example 34, the wall crossing system of Example 33 can optionally be configured such that the proximal end portion of the dilator is configured to engage with an actuator incorporated into a handle of the deflectable sheath. The actuator can be configured to control distal and proximal advancement of the dilator relative to the deflectable sheath.

Certain terms are used throughout this patent document to refer to particular features or components. As one skilled in the art appreciates, or will appreciate, different people may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to the treating clinician. "Distal" and "distally" refer to a position that is distant from, or in a direction away from, the treating clinician. "Proximal" and "proximally" refer to a position that is near, or in a direction toward, the treating clinician.

The scope of the present subject matter should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a system, device or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. An anatomical wall crossing system, comprising:
    a dilator extending from a proximal end portion to a distal end portion and including a lumen therethrough, the distal end portion including a dilator nose and a dilator beveled segment,
    wherein the dilator nose has a first outer diameter and a length of about 5-18 mm, inclusive,
    wherein the dilator beveled segment extends proximally of the dilator nose and tapers from a second outer diameter, greater than the first outer diameter, to the first outer diameter;
    a guidewire deliverable within the lumen of the dilator from a guidewire proximal end to a guidewire distal end, the guidewire distal end attached to a puncture needle having a needle body and a needle tip; and
    a tip sheath positioned around the puncture needle and configured to facilitate coaxial alignment of a needle body axis and a dilator axis;
    wherein the dilator includes a dilator stop configured to inhibit distal movement of the tip sheath from a position within the lumen of the dilator to a position external to the lumen of the dilator;
    wherein the tip sheath is configured to expand in diameter upon contact with the dilator stop as it is placed under compression, thereby releasing from the puncture needle.

2. The wall crossing system of claim 1, wherein the dilator nose includes a cylindrical cross-sectional shape having a wall thickness of about 0.0015-0.005 in, inclusive.

3. The wall crossing system of claim 2, wherein the dilator nose is formed from a thin-walled hypotube.

4. The wall crossing system of claim 1, wherein the dilator further includes a dilator alignment zone extending proximal of the dilator beveled segment and having a substantially uniform outer diameter.

5. The wall crossing system of claim 4, wherein the dilator further includes a dilator waist extending proximal of the dilator alignment zone and having a greater longitudinal flexibility than the dilator alignment zone.

6. The wall crossing system of claim 5, wherein the dilator waist has a length of about 5-50 mm, inclusive.

7. The wall crossing system of claim 5, wherein the dilator waist has an outer diameter that is 30-90%, inclusive, of an outer diameter of the dilator alignment zone.

8. The wall crossing system of claim 5, wherein the dilator waist is formed from a lower durometer polymer than a polymer of the dilator alignment zone.

9. The wall crossing system of claim 1, wherein an intermediate portion of the guidewire includes at least one looped segment.

10. The wall crossing system of claim 1, wherein the puncture needle has a length of 3-20 mm, inclusive.

11. The wall crossing system of claim 1, wherein the needle body has a needle body diameter of 0.001-0.004 in, inclusive, less than the lumen of the dilator to facilitate coaxial alignment of a needle body axis and a dilator axis.

12. The wall crossing system of claim 1, wherein the distal end of the guidewire is attached to a proximal end of the puncture needle at a hinge.

13. The wall crossing system of claim 12, wherein the hinge includes a shape memory material and, when unconstrained, forms an angle between the distal end of the guidewire and the proximal end of the puncture needle of 45-140 degrees, inclusive.

14. The wall crossing system of claim 12, wherein the hinge includes a cylindrical cross-sectional shape having a diameter less than a diameter of the guidewire and of the needle body.

15. The wall crossing system of claim 12, wherein the hinge includes a rectangular cross-sectional shape and is configured to bend in a direction defined by a plane of the at least one loop segment.

16. The wall crossing system of claim 1, further comprising a deflectable sheath.

17. The wall crossing system of claim 16, wherein the proximal end portion of the dilator is configured to engage with an actuator incorporated into a handle of the deflectable sheath, the actuator configured to control distal and proximal advancement of the dilator relative to the deflectable sheath.

\* \* \* \* \*